United States Patent
King et al.

(10) Patent No.: US 8,932,260 B2
(45) Date of Patent: *Jan. 13, 2015

(54) REDUCED-FRICTION CATHETER INTRODUCER AND METHOD OF MANUFACTURING AND USING THE SAME

(75) Inventors: Eric M. King, West Jordan, UT (US); Ronald Wortley, Salt Lake City, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 1874 days.

This patent is subject to a terminal disclaimer.

(21) Appl. No.: 11/531,339

(22) Filed: Sep. 13, 2006

(65) Prior Publication Data

US 2007/0123825 A1 May 31, 2007

Related U.S. Application Data

(63) Continuation-in-part of application No. 11/288,959, filed on Nov. 29, 2005.

(60) Provisional application No. 60/631,397, filed on Nov. 29, 2004.

(51) Int. Cl.
*A61M 5/178* (2006.01)
*A61M 25/06* (2006.01)
*A61M 25/00* (2006.01)

(52) U.S. Cl.
CPC ... *A61M 25/0668* (2013.01); *A61M 2025/0046* (2013.01)
USPC .................. 604/167.03; 604/164.05

(58) Field of Classification Search
CPC ..................... A61M 25/0668; A61M 25/0662; A61M 25/01; A61M 25/0102
USPC ......................... 604/164.01–170.03
See application file for complete search history.

(56) References Cited

U.S. PATENT DOCUMENTS 675,157 A 5/1901 Howard
2,908,283 A 10/1959 Kiffer et al.
(Continued)

FOREIGN PATENT DOCUMENTS

CN 103260694 A 8/2013
EP 0370721 A2 5/1990
(Continued)

OTHER PUBLICATIONS

Hazard Report—ECRI Problem Rerporting System, Health Devices, May-Jun. 1996; vol. 25, No. 5-6, pp. 214-215.
(Continued)

*Primary Examiner* — Matthew F Desanto
(74) *Attorney, Agent, or Firm* — Rutan & Tucker, LLP

(57) ABSTRACT

Tear-away and non-tear-away sheath introducers for catheters, methods for making such introducers, and methods for using such introducers are described. The sheath introducers contain movable valves that are encapsulated in a movable housing that allows the valve to move along the axis of the introducer. As the movable valve and housing travel along the axis, a portion of the hub protrudes past the valve and is exposed. As well, the sheath introducers can also contain a stationary valve and housing that can be opened to expose a portion of the hub when a conduit penetrates the stationary valve. In both instances, the protruding portion of the hub contains a friction-free pathway for a catheter into the sheath introducer. The introducers can therefore be used with any catheter, regardless of the size or material, because of the reduced or eliminated frictional force between the catheter and introducer.

17 Claims, 20 Drawing Sheets

(56) References Cited

U.S. PATENT DOCUMENTS

| | | | |
|---|---|---|---|
| 2,912,981 A | 11/1959 | Keough | |
| 3,176,690 A | 4/1965 | H'Doubler | |
| D217,795 S | 6/1970 | Spaven | |
| 3,612,050 A | 10/1971 | Sheridan | |
| 3,805,794 A | 4/1974 | Schlesinger | |
| 3,853,127 A | 12/1974 | Spademan | |
| 4,000,739 A | 1/1977 | Stevens | |
| 4,068,659 A | 1/1978 | Moorehead | |
| 4,089,506 A | 5/1978 | Blake | 251/196 |
| 4,143,853 A | 3/1979 | Abramson | |
| 4,198,973 A | 4/1980 | Millet | |
| 4,233,974 A | 11/1980 | Desecki et al. | |
| 4,296,747 A | 10/1981 | Ogle | |
| 4,306,562 A | 12/1981 | Osborne | |
| 4,387,879 A | 6/1983 | Tauschinski | |
| 4,411,654 A | 10/1983 | Boarini et al. | |
| 4,412,832 A | 11/1983 | Kling et al. | |
| 4,424,833 A | 1/1984 | Spector et al. | |
| 4,430,081 A | 2/1984 | Timmermans | |
| 4,431,426 A | 2/1984 | Groshong et al. | |
| 4,436,519 A | 3/1984 | O'Neill | |
| 4,445,893 A | 5/1984 | Bodicky | |
| 4,449,973 A | 5/1984 | Luther | |
| 4,453,928 A | 6/1984 | Steiger | |
| 4,468,224 A | 8/1984 | Enzmann et al. | |
| 4,473,067 A | 9/1984 | Schiff | 128/1 D |
| RE31,855 E | 3/1985 | Osborne | |
| 4,504,269 A | 3/1985 | Durand et al. | |
| 4,557,261 A | 12/1985 | Rugheimer | |
| 4,571,241 A | 2/1986 | Christopher | |
| 4,581,012 A | 4/1986 | Brown et al. | |
| 4,581,025 A | 4/1986 | Timmermans | |
| 4,588,398 A | 5/1986 | Daugherty et al. | |
| 4,591,355 A | 5/1986 | Hilse | |
| 4,596,559 A | 6/1986 | Fleischhacker | |
| 4,610,665 A | 9/1986 | Matsumoto et al. | |
| 4,610,671 A | 9/1986 | Luther | |
| 4,619,643 A | 10/1986 | Bai | |
| 4,626,245 A | 12/1986 | Weinstein | |
| 4,634,432 A | 1/1987 | Kocak | |
| 4,650,472 A | 3/1987 | Bates | |
| 4,654,031 A | 3/1987 | Lentz | |
| 4,657,772 A | 4/1987 | Kocak | |
| 4,673,393 A | 6/1987 | Suzuki et al. | |
| 4,701,159 A | 10/1987 | Brown et al. | |
| 4,705,511 A | 11/1987 | Kocak | |
| 4,722,725 A | 2/1988 | Sawyer et al. | |
| 4,723,550 A | 2/1988 | Bales et al. | |
| 4,726,374 A | 2/1988 | Bales et al. | |
| 4,743,265 A | 5/1988 | Whitehouse et al. | |
| 4,747,833 A | 5/1988 | Kousai et al. | |
| 4,748,982 A | 6/1988 | Horzewski et al. | |
| 4,753,765 A | 6/1988 | Pande | |
| 4,772,266 A | 9/1988 | Groshong | |
| 4,784,644 A | 11/1988 | Sawyer et al. | |
| 4,795,426 A | 1/1989 | Jones | |
| 4,798,594 A | 1/1989 | Hillstead | |
| 4,809,679 A | 3/1989 | Shimonaka et al. | |
| 4,842,591 A | 6/1989 | Luther | |
| 4,842,592 A | 6/1989 | Caggiani et al. | |
| 4,865,593 A | 9/1989 | Ogawa et al. | |
| 4,895,565 A | 1/1990 | Hillstead | |
| 4,909,798 A | 3/1990 | Fleischhacker et al. | |
| 4,921,479 A | 5/1990 | Grayzel | |
| 4,929,235 A | 5/1990 | Merry et al. | |
| 4,929,236 A | 5/1990 | Sampson | |
| 4,932,633 A | 6/1990 | Johnson et al. | |
| 4,935,010 A * | 6/1990 | Cox et al. | 604/122 |
| 4,936,826 A | 6/1990 | Amarasinghe | |
| 4,946,133 A | 8/1990 | Johnson et al. | |
| 4,952,359 A | 8/1990 | Wells | |
| 4,956,755 A | 9/1990 | Maglica et al. | |
| 4,960,412 A | 10/1990 | Fink | |
| 4,966,588 A | 10/1990 | Rayman et al. | |
| 4,973,312 A | 11/1990 | Andrew | |
| 4,983,168 A | 1/1991 | Moorehead | |
| 4,994,027 A | 2/1991 | Farrell | 604/53 |
| 4,997,424 A | 3/1991 | Little | |
| 5,000,745 A | 3/1991 | Guest et al. | |
| 5,007,901 A | 4/1991 | Shields | |
| 5,009,391 A | 4/1991 | Steigerwald | |
| 5,011,478 A | 4/1991 | Cope | |
| 5,035,686 A | 7/1991 | Crittenden et al. | |
| 5,041,095 A | 8/1991 | Littrell | |
| 5,053,014 A | 10/1991 | Van Heugten | |
| 5,064,414 A | 11/1991 | Revane | |
| 5,066,285 A | 11/1991 | Hillstead | |
| 5,071,411 A | 12/1991 | Hillstead | |
| 5,078,688 A | 1/1992 | Lobodzinski et al. | |
| 5,085,645 A | 2/1992 | Purdy et al. | |
| 5,092,857 A | 3/1992 | Fleischhacker | |
| 5,098,392 A | 3/1992 | Fleischhacker et al. | |
| 5,098,393 A | 3/1992 | Amplatz et al. | |
| 5,102,395 A | 4/1992 | Cheer et al. | |
| 5,104,389 A | 4/1992 | Deem et al. | |
| 5,106,054 A | 4/1992 | Mollenauer et al. | |
| 5,112,301 A | 5/1992 | Fenton, Jr. et al. | |
| 5,114,408 A | 5/1992 | Fleischhaker et al. | |
| 5,117,836 A | 6/1992 | Millar | |
| 5,125,903 A | 6/1992 | McLaughlin et al. | |
| 5,125,904 A | 6/1992 | Lee | |
| 5,141,497 A | 8/1992 | Erskine | |
| 5,149,327 A | 9/1992 | Oshiyama et al. | |
| 5,154,701 A | 10/1992 | Cheer et al. | |
| 5,156,596 A * | 10/1992 | Balbierz et al. | 604/164.11 |
| 5,158,545 A | 10/1992 | Trudell et al. | |
| 5,160,323 A | 11/1992 | Andrew et al. | |
| 5,163,903 A | 11/1992 | Crittenden et al. | |
| 5,167,634 A | 12/1992 | Corrigan, Jr. et al. | |
| 5,167,637 A | 12/1992 | Okada et al. | |
| 5,169,393 A | 12/1992 | Moorehead et al. | |
| 5,171,222 A | 12/1992 | Euteneuer et al. | |
| 5,176,652 A | 1/1993 | Littrell | |
| 5,180,372 A | 1/1993 | Vegoe et al. | |
| 5,190,529 A | 3/1993 | McCrory et al. | |
| 5,191,898 A | 3/1993 | Millar | |
| 5,197,976 A | 3/1993 | Herweck et al. | |
| 5,201,722 A | 4/1993 | Moorehead et al. | |
| 5,205,834 A | 4/1993 | Moorehead et al. | |
| 5,207,649 A | 5/1993 | Aruny | |
| 5,211,633 A | 5/1993 | Stouder, Jr. | |
| 5,215,538 A | 6/1993 | Larkin | |
| 5,221,263 A | 6/1993 | Sinko et al. | 604/161 |
| 5,224,930 A | 7/1993 | Spaeth et al. | |
| 5,234,407 A | 8/1993 | Teirstein et al. | |
| 5,234,410 A | 8/1993 | Graham et al. | |
| 5,234,438 A | 8/1993 | Semrad | |
| 5,242,413 A | 9/1993 | Heiliger | |
| 5,242,430 A | 9/1993 | Arenas et al. | |
| 5,242,431 A | 9/1993 | Kristiansen | 604/283 |
| 5,250,033 A | 10/1993 | Evans et al. | 604/160 |
| 5,255,691 A | 10/1993 | Otten | |
| 5,269,771 A | 12/1993 | Thomas et al. | |
| 5,273,540 A | 12/1993 | Luther et al. | |
| 5,273,546 A | 12/1993 | McLaughlin et al. | |
| 5,275,583 A | 1/1994 | Crainich | |
| 5,279,597 A | 1/1994 | Dassa et al. | |
| 5,290,294 A | 3/1994 | Cox et al. | |
| 5,292,311 A | 3/1994 | Cope | |
| 5,304,142 A | 4/1994 | Liebl et al. | |
| 5,304,156 A | 4/1994 | Sylvanowicz et al. | |
| 5,306,240 A | 4/1994 | Berry | |
| 5,312,355 A | 5/1994 | Lee | |
| 5,312,357 A | 5/1994 | Buijs et al. | |
| 5,318,542 A | 6/1994 | Hirsch et al. | |
| 5,320,602 A | 6/1994 | Karpiel | |
| 5,324,271 A | 6/1994 | Abiuso et al. | |
| 5,334,157 A | 8/1994 | Klein et al. | |
| 5,334,187 A | 8/1994 | Fischell et al. | |
| 5,336,192 A | 8/1994 | Palestrant | |
| 5,348,537 A | 9/1994 | Wiesner et al. | |
| 5,350,362 A | 9/1994 | Stouder, Jr. | |
| 5,350,363 A | 9/1994 | Goode et al. | |
| 5,364,393 A | 11/1994 | Auth et al. | |

(56) References Cited

U.S. PATENT DOCUMENTS

| | | | |
|---|---|---|---|
| 5,368,574 A | 11/1994 | Antonacci et al. | |
| 5,382,241 A | 1/1995 | Choudhury et al. | |
| 5,389,081 A | 2/1995 | Castro | 604/167 |
| 5,389,090 A | 2/1995 | Fischell et al. | |
| 5,391,152 A | 2/1995 | Patterson | |
| 5,395,352 A | 3/1995 | Penny | |
| 5,397,310 A | 3/1995 | Chu et al. | |
| 5,397,311 A | 3/1995 | Walker et al. | 604/160 |
| 5,405,320 A | 4/1995 | Twardowski et al. | |
| 5,405,323 A * | 4/1995 | Rogers et al. | 604/508 |
| 5,405,329 A | 4/1995 | Durand et al. | |
| 5,409,463 A | 4/1995 | Thomas et al. | |
| 5,409,464 A | 4/1995 | Villalobos | |
| 5,409,469 A | 4/1995 | Schaerf | |
| 5,413,561 A | 5/1995 | Fischell et al. | |
| 5,419,340 A | 5/1995 | Stevens | |
| 5,423,762 A | 6/1995 | Hillstead | |
| 5,429,616 A | 7/1995 | Schaffer | |
| 5,437,645 A | 8/1995 | Urban et al. | |
| 5,441,504 A | 8/1995 | Pohndorf et al. | 606/129 |
| 5,453,095 A | 9/1995 | Davila et al. | |
| 5,460,616 A | 10/1995 | Weinstein et al. | |
| 5,466,230 A | 11/1995 | Davila | |
| 5,472,418 A | 12/1995 | Palestrant | |
| 5,472,435 A | 12/1995 | Sutton | |
| 5,474,099 A | 12/1995 | Boehmer et al. | |
| 5,474,544 A | 12/1995 | Lynn | |
| 5,484,401 A | 1/1996 | Rodriguez et al. | |
| 5,488,960 A | 2/1996 | Toner | |
| 5,489,269 A | 2/1996 | Aldrich et al. | |
| 5,489,273 A | 2/1996 | Whitney et al. | |
| 5,496,346 A | 3/1996 | Horzewski et al. | |
| 5,499,975 A | 3/1996 | Cope et al. | |
| 5,501,676 A | 3/1996 | Niedospial et al. | |
| 5,509,897 A | 4/1996 | Twardowski et al. | |
| 5,520,655 A | 5/1996 | Davila et al. | |
| 5,520,663 | 5/1996 | Patterson et al. | |
| 5,536,255 A | 7/1996 | Moss | |
| 5,538,505 A | 7/1996 | Weinstein et al. | |
| 5,549,651 A | 8/1996 | Lynn | |
| 5,556,387 A | 9/1996 | Mollenauer et al. | 604/249 |
| 5,558,652 A | 9/1996 | Henke | |
| 5,599,305 A | 2/1997 | Hermann et al. | |
| 5,603,702 A | 2/1997 | Smith et al. | |
| 5,613,663 A * | 3/1997 | Schmidt et al. | 251/149.2 |
| 5,613,953 A | 3/1997 | Pohndorf | 604/165 |
| 5,613,956 A | 3/1997 | Patterson et al. | |
| 5,647,857 A | 7/1997 | Anderson et al. | |
| 5,653,697 A | 8/1997 | Quiachon et al. | 604/280 |
| 5,653,698 A | 8/1997 | Niedospial et al. | |
| 5,657,963 A | 8/1997 | Hinchliffe et al. | |
| 5,662,606 A | 9/1997 | Cimino et al. | 604/95 |
| 5,672,158 A | 9/1997 | Okada et al. | |
| 5,685,856 A | 11/1997 | Lehrer | |
| 5,685,858 A | 11/1997 | Kawand | 604/171 |
| 5,702,370 A | 12/1997 | Sylvanowicz et al. | |
| 5,713,867 A | 2/1998 | Morris | |
| 5,727,770 A | 3/1998 | Dennis | |
| 5,735,819 A | 4/1998 | Elliott | |
| 5,741,233 A | 4/1998 | Riddle et al. | |
| 5,741,234 A | 4/1998 | Aboul-Hosn | 604/174 |
| 5,752,937 A | 5/1998 | Otten et al. | |
| 5,755,693 A | 5/1998 | Walker et al. | |
| 5,755,702 A | 5/1998 | Hillstead et al. | |
| 5,766,203 A | 6/1998 | Imran et al. | |
| 5,772,678 A | 6/1998 | Thomason et al. | |
| 5,782,807 A | 7/1998 | Falvai et al. | |
| 5,782,812 A | 7/1998 | Hart et al. | |
| 5,782,817 A | 7/1998 | Franzel et al. | |
| 5,800,414 A | 9/1998 | Cazal et al. | |
| 5,807,350 A | 9/1998 | Diaz | |
| 5,817,069 A | 10/1998 | Arnett | |
| 5,843,031 A | 12/1998 | Hermann et al. | |
| 5,853,393 A | 12/1998 | Bogert | |
| 5,858,007 A | 1/1999 | Fagan et al. | |
| 5,879,333 A | 3/1999 | Smith et al. | |
| 5,885,217 A | 3/1999 | Gisselberg et al. | |
| 5,895,376 A | 4/1999 | Schwartz et al. | |
| 5,911,710 A * | 6/1999 | Barry et al. | 604/249 |
| 5,916,194 A | 6/1999 | Jacobsen et al. | |
| 5,919,160 A | 7/1999 | Sanfilippo, II | |
| 5,921,968 A | 7/1999 | Lampropoulos et al. | |
| 5,935,112 A | 8/1999 | Stevens et al. | |
| 5,935,122 A | 8/1999 | Fourkas et al. | |
| 5,944,695 A | 8/1999 | Johnson et al. | |
| 5,951,518 A | 9/1999 | Licata et al. | |
| 5,957,912 A | 9/1999 | Heitzmann | |
| 5,967,490 A | 10/1999 | Pike | |
| 5,971,958 A | 10/1999 | Zhang | |
| 5,997,562 A | 12/1999 | Zadno-Azizi et al. | |
| 6,017,352 A | 1/2000 | Nash et al. | |
| 6,024,729 A | 2/2000 | Dehdashtian et al. | |
| 6,027,480 A | 2/2000 | Davis et al. | |
| 6,033,375 A | 3/2000 | Brumbach | |
| 6,033,388 A | 3/2000 | Nordstrom et al. | |
| 6,053,904 A | 4/2000 | Scribner et al. | |
| 6,074,377 A | 6/2000 | Sanfilippo, II | |
| 6,080,141 A | 6/2000 | Castro et al. | |
| 6,083,207 A | 7/2000 | Heck | 604/256 |
| 6,086,570 A | 7/2000 | Aboul-Hosn et al. | |
| 6,088,889 A | 7/2000 | Luther et al. | |
| 6,106,540 A | 8/2000 | White et al. | |
| 6,120,476 A | 9/2000 | Fung et al. | |
| 6,120,480 A | 9/2000 | Zhang et al. | |
| 6,120,494 A | 9/2000 | Jonkman | |
| 6,142,981 A | 11/2000 | Heck et al. | |
| 6,156,054 A | 12/2000 | Zadno-Azizi et al. | |
| 6,159,198 A | 12/2000 | Gardeski et al. | |
| 6,162,196 A | 12/2000 | Hart et al. | |
| 6,171,281 B1 | 1/2001 | Zhang | |
| 6,210,366 B1 | 4/2001 | Sanfilippo, II | |
| 6,213,988 B1 | 4/2001 | McIvor et al. | |
| 6,221,057 B1 | 4/2001 | Schwartz et al. | |
| 6,228,062 B1 | 5/2001 | Howell et al. | |
| 6,251,119 B1 | 6/2001 | Addis | |
| 6,258,058 B1 | 7/2001 | Sanfilippo, II | |
| 6,273,871 B1 | 8/2001 | Davis et al. | |
| 6,276,661 B1 | 8/2001 | Laird | |
| 6,277,108 B1 | 8/2001 | McBroom et al. | |
| 6,287,280 B1 | 9/2001 | Lampropoulos et al. | |
| D450,839 S | 11/2001 | Junker | |
| 6,322,541 B2 | 11/2001 | West et al. | |
| 6,331,176 B1 | 12/2001 | Becker et al. | |
| 6,338,725 B1 | 1/2002 | Hermann et al. | |
| 6,352,520 B1 | 3/2002 | Miyazaki et al. | |
| 6,358,460 B1 | 3/2002 | Hunt, Jr. et al. | |
| 6,361,559 B1 | 3/2002 | Houser | |
| 6,375,157 B1 | 4/2002 | Van de Lande | 251/327 |
| 6,402,723 B1 | 6/2002 | Lampropoulos et al. | |
| 6,413,250 B1 | 7/2002 | Smith et al. | |
| 6,416,499 B2 | 7/2002 | Paul, Jr. | |
| 6,454,744 B1 | 9/2002 | Spohn et al. | |
| 6,458,103 B1 | 10/2002 | Albert et al. | |
| 6,494,860 B2 | 12/2002 | Rocamora et al. | |
| 6,497,681 B1 | 12/2002 | Brenner | |
| 6,508,790 B1 | 1/2003 | Lawrence | |
| 6,520,939 B2 | 2/2003 | Lafontaine | |
| 6,544,247 B1 | 4/2003 | Gardeski et al. | |
| 6,551,283 B1 | 4/2003 | Guo et al. | |
| 6,575,960 B2 * | 6/2003 | Becker et al. | 604/533 |
| 6,589,214 B2 | 7/2003 | McGuckin, Jr. et al. | |
| 6,589,262 B1 | 7/2003 | Honebrink et al. | |
| 6,592,544 B1 | 7/2003 | Mooney et al. | |
| 6,592,553 B2 | 7/2003 | Zhang et al. | |
| 6,595,959 B1 | 7/2003 | Stratienko | |
| 6,599,302 B2 | 7/2003 | Houser | |
| 6,623,460 B1 | 9/2003 | Heck | 604/256 |
| 6,632,200 B2 | 10/2003 | Guo et al. | |
| 6,632,234 B2 | 10/2003 | Kieturakis | |
| 6,638,242 B2 | 10/2003 | Wilson et al. | |
| 6,641,564 B1 | 11/2003 | Kraus | 604/164.1 |
| 6,645,178 B1 | 11/2003 | Junker et al. | |
| 6,652,492 B1 | 11/2003 | Bell et al. | |
| 6,655,660 B2 | 12/2003 | Wales | 251/319 |

(56) References Cited

U.S. PATENT DOCUMENTS

| | | | |
|---|---|---|---|
| 6,663,595 B2 | 12/2003 | Spohn et al. | |
| 6,666,853 B2 | 12/2003 | Chu et al. | 604/533 |
| 6,682,498 B2 | 1/2004 | Ross | |
| 6,682,519 B1 | 1/2004 | Schon | |
| 6,692,464 B2 | 2/2004 | Graf | 604/160 |
| 6,695,810 B2 | 2/2004 | Peacock | |
| 6,695,832 B2 | 2/2004 | Schon et al. | |
| 6,712,789 B1 | 3/2004 | Lange et al. | 604/164.02 |
| 6,712,791 B2 | 3/2004 | Lui | |
| 6,719,749 B1 | 4/2004 | Schweikert et al. | |
| 6,740,101 B2 | 5/2004 | Houser | |
| 6,776,774 B2 | 8/2004 | Tansey, Jr. et al. | |
| 6,796,991 B2 | 9/2004 | Nardeo | 606/191 |
| 6,808,502 B2 | 10/2004 | Nguyen | |
| 6,808,509 B1 | 10/2004 | Davey | 604/167.04 |
| 6,808,520 B1 | 10/2004 | Fourkas | |
| 6,814,718 B2 | 11/2004 | Mcguckin | |
| 6,827,709 B2 | 12/2004 | Fujii | |
| 6,827,710 B1 | 12/2004 | Mooney et al. | |
| 6,872,198 B1 | 3/2005 | Wilson et al. | |
| 6,881,211 B2 | 4/2005 | Schweikert et al. | |
| 6,887,220 B2 | 5/2005 | Hogendijk | |
| 6,887,417 B1 | 5/2005 | Gawreluk et al. | |
| 6,913,594 B2 | 7/2005 | Coleman et al. | 604/95.04 |
| 6,916,313 B2 | 7/2005 | Cunningham | |
| 6,966,886 B2 | 11/2005 | Appling | |
| 7,001,396 B2 | 2/2006 | Glazier et al. | |
| 7,017,886 B1 | 3/2006 | Ngene-Igwe | 251/326 |
| 7,100,690 B2 | 9/2006 | Mullen et al. | |
| 7,100,890 B2 | 9/2006 | Cote, Sr. et al. | |
| 7,101,353 B2 | 9/2006 | Lui et al. | |
| 7,166,088 B2 | 1/2007 | Heuser | |
| 7,192,433 B2 * | 3/2007 | Osypka et al. | 606/108 |
| 7,294,296 B2 | 11/2007 | Davey | |
| 7,524,305 B2 | 4/2009 | Moyer | |
| 7,637,893 B2 | 12/2009 | Christensen et al. | |
| 8,105,315 B2 | 1/2012 | Johnson et al. | |
| 8,403,890 B2 | 3/2013 | King et al. | |
| 8,720,065 B2 | 5/2014 | Christensen et al. | |
| 2001/0001813 A1 | 5/2001 | West et al. | |
| 2001/0041872 A1 | 11/2001 | Paul | |
| 2001/0041873 A1 | 11/2001 | Dopper et al. | |
| 2001/0041875 A1 | 11/2001 | Higuchi et al. | |
| 2001/0049499 A1 | 12/2001 | Lui et al. | |
| 2002/0010425 A1 | 1/2002 | Guo et al. | |
| 2002/0038106 A1 | 3/2002 | Fujii | |
| 2002/0055715 A1 | 5/2002 | Young et al. | |
| 2002/0068898 A1 | 6/2002 | McGuckin et al. | |
| 2002/0068899 A1 | 6/2002 | McGuckin et al. | |
| 2002/0072789 A1 | 6/2002 | Hackett | |
| 2002/0107482 A1 | 8/2002 | Rocamora et al. | |
| 2002/0128604 A1 * | 9/2002 | Nakajima | 604/164.01 |
| 2003/0014015 A1 | 1/2003 | Tansey et al. | |
| 2003/0050604 A1 | 3/2003 | Lui et al. | |
| 2003/0163139 A1 | 8/2003 | Graf | |
| 2003/0216771 A1 | 11/2003 | Osypka et al. | |
| 2004/0006330 A1 | 1/2004 | Fangrow | |
| 2004/0030319 A1 | 2/2004 | Korkor et al. | |
| 2004/0049499 A1 | 3/2004 | Nomoto et al. | |
| 2004/0059296 A1 | 3/2004 | Godfrey | |
| 2004/0065333 A1 | 4/2004 | Wilson et al. | |
| 2004/0082913 A1 | 4/2004 | Spohn et al. | |
| 2004/0092863 A1 | 5/2004 | Raulerson et al. | |
| 2004/0092879 A1 | 5/2004 | Kraus et al. | |
| 2004/0097863 A1 | 5/2004 | Appling | |
| 2004/0097903 A1 | 5/2004 | Raulerson | |
| 2004/0103229 A1 | 5/2004 | Callum | |
| 2004/0122418 A1 | 6/2004 | Voorhees | |
| 2004/0158208 A1 | 8/2004 | Hiejima | |
| 2004/0167478 A1 | 8/2004 | Mooney et al. | |
| 2004/0171997 A1 | 9/2004 | Wilson et al. | |
| 2004/0172003 A1 | 9/2004 | Wilson et al. | |
| 2004/0176739 A1 | 9/2004 | Stephens et al. | |
| 2004/0176744 A1 | 9/2004 | Lange et al. | |
| 2004/0176781 A1 * | 9/2004 | Lindstrom et al. | 606/129 |
| 2004/0186444 A1 | 9/2004 | Daly et al. | |
| 2004/0193112 A1 | 9/2004 | Glazier et al. | |
| 2004/0193119 A1 | 9/2004 | Canaud et al. | |
| 2004/0243095 A1 | 12/2004 | Nimkar et al. | |
| 2004/0254534 A1 | 12/2004 | Bjorkman et al. | |
| 2004/0254541 A1 | 12/2004 | Wong et al. | |
| 2004/0260243 A1 | 12/2004 | Rickerd | 604/161 |
| 2004/0267202 A1 | 12/2004 | Potter | |
| 2005/0010238 A1 | 1/2005 | Potter et al. | |
| 2005/0027257 A1 | 2/2005 | Davey | |
| 2005/0049555 A1 | 3/2005 | Moorehead et al. | |
| 2005/0049628 A1 | 3/2005 | Schweikert et al. | |
| 2005/0090779 A1 | 4/2005 | Osypka | |
| 2005/0113805 A1 | 5/2005 | Devellian et al. | |
| 2005/0149060 A1 | 7/2005 | Thorstenson et al. | |
| 2005/0245874 A1 | 11/2005 | Carrez et al. | |
| 2005/0257838 A1 | 11/2005 | Enerson | |
| 2005/0267487 A1 | 12/2005 | Christensen et al. | 606/108 |
| 2006/0030817 A1 | 2/2006 | Kraus et al. | |
| 2006/0052749 A1 | 3/2006 | Moyer | |
| 2006/0149293 A1 | 7/2006 | King | |
| 2007/0135794 A1 | 6/2007 | Raulerson et al. | |
| 2008/0051717 A1 | 2/2008 | Voss et al. | |
| 2008/0097386 A1 | 4/2008 | Osypka | |
| 2008/0108976 A1 | 5/2008 | Johnson et al. | |
| 2008/0300538 A1 | 12/2008 | Schweikert et al. | |
| 2009/0105652 A1 | 4/2009 | Beal et al. | |
| 2009/0131873 A1 | 5/2009 | Spear et al. | |
| 2009/0143739 A1 | 6/2009 | Nardeo et al. | |
| 2009/0177163 A1 | 7/2009 | King et al. | |
| 2009/0218728 A1 | 9/2009 | Moyer | |
| 2009/0234290 A1 | 9/2009 | Fisher et al. | |
| 2009/0299291 A1 | 12/2009 | Baid | |
| 2010/0094226 A1 | 4/2010 | Helgeson et al. | |
| 2010/0101069 A1 | 4/2010 | Christensen et al. | |
| 2012/0143138 A1 | 6/2012 | King et al. | |
| 2012/0184913 A1 | 7/2012 | Christensen et al. | |
| 2013/0226141 A1 | 8/2013 | King et al. | |

FOREIGN PATENT DOCUMENTS

| | | | |
|---|---|---|---|
| EP | 0442194 A2 | 8/1991 | |
| EP | 1240916 A1 | 9/2002 | |
| IN | 2762/DELNP/2010 | 10/2011 | |
| JP | 2007511089 T | 4/2007 | |
| WO | 9813083 A1 | 4/1998 | |
| WO | 0149363 A1 | 7/2001 | |
| WO | WO 2004/103229 | 12/2004 | A61F 5/44 |
| WO | 2005107843 A1 | 11/2005 | |
| WO | 2007046850 A2 | 4/2007 | |
| WO | 2007050788 A2 | 5/2007 | |
| WO | 2007052278 A2 | 5/2007 | |
| WO | 2009052327 A1 | 4/2009 | |
| WO | 2009097274 A2 | 8/2009 | |
| WO | 2009114456 A1 | 9/2009 | |
| WO | 2012083245 A1 | 6/2012 | |

OTHER PUBLICATIONS

PCT/US2005/015253 filed May 2, 2005 Preliminary Report on Patentability dated Nov. 1, 2006.

PCT/US2005/015253 filed May 2, 2005 Search Report dated Aug. 4, 2005.

PCT/US2005/015253 filed May 2, 2005 Written Opinion dated Aug. 4, 2005.

PCT/US2008/080227 filed Oct. 16, 2008 Preliminary Report on Patentability dated Apr. 20, 2010.

PCT/US2008/080227 filed Oct. 16, 2008 Search Report dated Dec. 23, 2008.

PCT/US2008/080227 filed Oct. 16, 2008 Written Opinion dated Dec. 23, 2008.

PCT/US2010/026409 filed Mar. 5, 2010 Search Report dated Apr. 27, 2010.

PCT/US2010/026409 filed Mar. 5, 2010 Written Opinion dated Apr. 27, 2010.

U.S. Appl. No. 11/288,959, filed Nov. 29, 2005 Final Office Action dated Jun. 22, 2009.

(56) References Cited

OTHER PUBLICATIONS

U.S. Appl. No. 11/288,959, filed Nov. 29, 2005 Non-Final Office Action dated Oct. 20, 2008.
U.S. Appl. No. 12/252,975, filed Oct. 16, 2008 Non-Final Office Action dated Sep. 8, 2010.
U.S. Appl. No. 12/648,533, filed Dec. 29, 2009 Non-Final Office Action dated Sep. 13, 2010.
PCT/US2010/026409 filed Mar. 5, 2010 International Preliminary Report on Patentability dated Apr. 27, 2010.
U.S. Appl. No. 12/252,975, filed Oct. 16, 2008 Final Office Action dated Jan. 19, 2011.
U.S. Appl. No. 12/648,533, filed Dec. 29, 2009 Final Office Action dated Jan. 19, 2011.
CN 200880121184.X filed Oct. 16, 2008 Office Action dated Feb. 16, 2012.
PCT/US2011/065632 filed Dec. 16, 2011 International Search Report dated Apr. 4, 2012.
PCT/US2011/065632 filed Dec. 16, 2011 Written Opinion dated Apr. 4, 2012.
U.S. Appl. No. 12/399,749, filed Mar. 6, 2009 Non-Final Office Action dated Mar. 28, 2012.
CN 200880121184.X filed Oct. 16, 2008 Office Action dated Aug. 20, 2012.
U.S. Appl. No. 12/252,975, filed Oct. 16, 2008 Final Office Action dated Nov. 8, 2012.
U.S. Appl. No. 12/252,975, filed Oct. 16, 2008 Non-Final Office Action dated Apr. 11, 2012.
U.S. Appl. No. 12/252,975, filed Oct. 16, 2008 Notice of Panel Decision dated Dec. 9, 2011.
U.S. Appl. No. 12/399,749, filed Mar. 6, 2009 Final Office Action dated Oct. 11, 2012.
U.S. Appl. No. 12/648,533, filed Dec. 29, 2009 Examiner's Answer dated Dec. 22, 2011.
U.S. Appl. No. 12/648,533, filed Dec. 29, 2009 Notice of Panel Decision dated Jun. 16, 2011.
CN 200880121184.X filed Oct. 16, 2008 Decision of Rejection dated Dec. 4, 2012.
PCT/US2011/065632 filed Dec. 16, 2011 International Preliminary Report on Patentability dated Jun. 18, 2013.
U.S. Appl. No. 11/288,959, filed Nov. 29, 2005 Non-Final Office Action dated Mar. 29, 2013.
U.S. Appl. No. 11/288,959, filed Nov. 29, 2005 Advisory Action dated Feb. 28, 2014.
U.S. Appl. No. 11/288,959, filed Nov. 29, 2005 Final Office Action dated Dec. 6, 2013.
U.S. Appl. No. 12/252,975, filed Oct. 16, 2008 Notice of Allowance dated Aug. 20, 2013.
U.S. Appl. No. 13/329,141, filed Dec. 16, 2011 Non-Final Office Action dated Feb. 14, 2014.
U.S. Appl. No. 13/434,415, filed Mar. 29, 2012 Non-Final Office Action dated Aug. 15, 2013.
U.S. Appl. No. 13/434,415, filed Mar. 29, 2012 Notice of Allowance dated Dec. 26, 2013.
EP 08840257.3 Extended European Search Report dated Aug. 12, 2014.
EP 11848156.3 filed Jul. 16, 2013 extended European search report dated May 2, 2014.
U.S. Appl. No. 13/329,141, filed Dec. 16, 2011 Advisory Action dated Jul. 11, 2014.
U.S. Appl. No. 13/329,141, filed Dec. 16, 2011 Final Office Action dated May 8, 2014.
U.S. Appl. No. 13/849,261, filed Mar. 22, 2013 Non-Final Office Action dated Aug. 5, 2014.

* cited by examiner

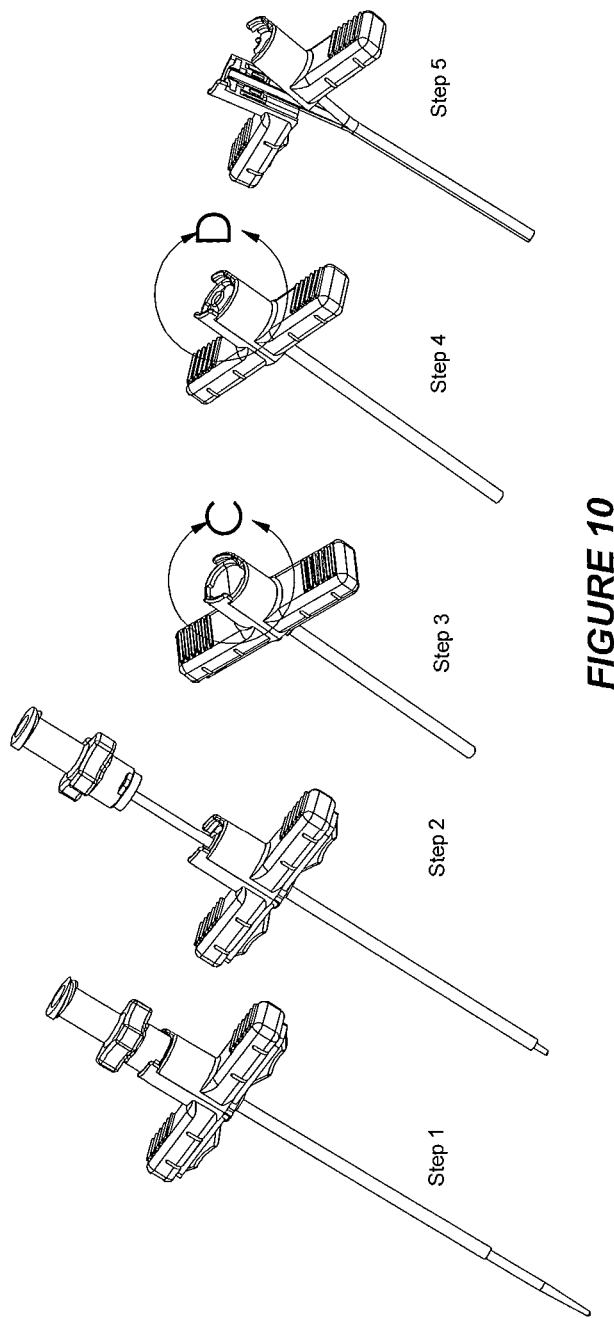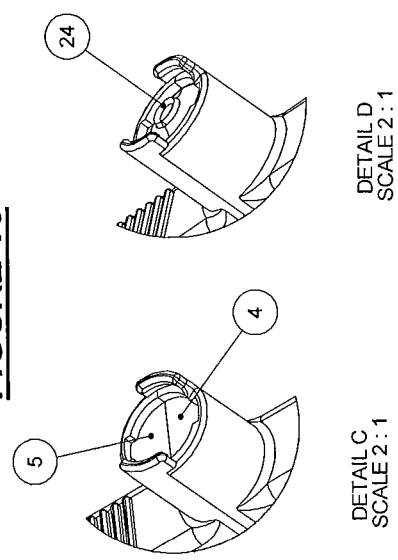
FIGURE 10

US 8,932,260 B2

REDUCED-FRICTION CATHETER INTRODUCER AND METHOD OF MANUFACTURING AND USING THE SAME

REFERENCE TO RELATED APPLICATIONS

This application is a continuation-in-part of U.S. patent application Ser. No. 11/288,959, filed on Nov. 29, 2005, which claims priority to U.S. Provisional Application No. 60/631,397, filed on Nov. 29, 2004, the disclosures of which are incorporated herein by reference.

FIELD OF THE INVENTION

The invention relates to medical devices and methods for manufacturing such medical devices. In particular, the invention relates to introducers for catheters, methods for making such introducers, and methods for using such introducers. More particularly, the invention relates to self-sealing sheath introducers (both tear-away and non-tear-away), methods for manufacturing such introducers, and methods of using such introducers in medical procedures.

BACKGROUND OF THE INVENTION

Tear-away sheath introducers ("sheath introducers" or "introducers") and their use as medical devices are well known in the art. See, for example U.S. Pat. Nos. 6,814,718, 6,808,520, 6,808,509, 6,796,991, 6,740,101, 6,712,791, 6,712,789, 6,695,810, 6,641,564, 6,632,234, 6,623,460, 6,599,302, 6,361,559, and 5,558,652, as well as U.S. Patent Applications Ser. Nos. 20040260243, 20040254534, 20040176781, 2004006330, 2004097863, and 2002072789, the disclosures of which are incorporated herein by reference. These introducers are used in medical procedures to insert a catheter into the body and provide vascular access to the vessel of a patient. The catheters are inserted via the introducers by first using a needle to create an access site. A dilator is then used to dilate the access site to allow a larger-diameter sheath introducer to be introduced into the vessel through the access site. The catheter is then inserted through the sheath introducer and into the vessel. After the catheter has been inserted, the sheath introducer is removed, leaving the catheter in the vessel.

As shown in FIG. 19, conventional tear-away (or split) sheath introducers 100 usually contain four major components: (1) a dilator 140; (2) a tear-away sheath hub 111; (3) a tear-away valve 113; and (4) a tear-away sheath 130. The dilator 140 facilitates insertion of the sheath introducer 100 into the vascular system and maintains the inside diameter of the sheath 130 during insertion. The dilator 140 is normally locked into the hub 111 in order to keep it seated within the sheath 130. The dilator 140 typically contains a tapered tip to facilitate insertion into the vascular system with the proximal end 144 of the dilator 140 containing a standard medical luer hub 146. Both the distal end 142 and the proximal end 144 of the dilator 140 are usually manufactured of a rigid polymer.

The tear-away hub 111 provides a means to contain the valve 113 while connecting the valve 113 and the sheath 130. The hub 111 typically has a "T" shape with the opposing ends of the "T" being grasped and pulled to split both the valve 113 and sheath 130. Thus, the hub 111 provides a mechanism to split the sheath 130 into two portions and allow the introducer to be split and removed from around the catheter. The hub 111 also often manufactured of a rigid polymer.

The tear-away valve 113, however, is typically made of a flexible material (such as silicone) that provides a self-sealing slit. The valve 113 may be designed as one piece that tears in half during the splitting procedure, or as two (or more) pieces that separate from each other during the splitting procedure. With conventional introducers, the valve 113 is encapsulated by the hub 111.

The tear-away sheath 130 is normally manufactured as a thin-walled structure, often as an extrusion. The extrusion contains splitting means, i.e., score lines that facilitate splitting or a self-splitting propagating material (such as linearly-directional extrusion). The proximal end 132 of the sheath 130 is attached to the hub 111 using over-molding or any other known attachment mechanism. The distal end 134 of the sheath 130 can be tapered to provide a smooth transition at the dilator/sheath interface.

To use the introducer 100, it is inserted in the desired vessel. Then the dilator 140 is unlocked from the hub 111 and removed to allow room for a catheter (or any similar medical device) to be inserted into the sheath. The valve 113 remains stationary inside the hub 111 and blocks air and/or fluid from flowing through the sheath 130 and hub 111 when they are left behind after the dilator is removed. The valve 113 keeps the passage 105 clear until a catheter is inserted into the passage 105 through the valve.

The introducer 100 is typically used for larger catheters, i.e., those with a diameter of 12 to 16 French. These larger-diameter introducers are rigid due to their diameter and the material used to construct them. This rigidity allows the large catheters to overcome the frictional forces needed to push the catheter through the valve.

But inserting smaller catheters into smaller introducers is more difficult. Typical introducers designed for smaller catheters (i.e., those 3 to 12 French in diameter) are made with open communication between the access site and the vascular system once the dilator is removed. This open configuration exists because smaller catheters, due to their smaller diameter and material, are not rigid enough to overcome the frictional forces needed to push the catheter through the valve. In other words, it is like trying to "push" a rope through a hole: the rope (i.e., catheter) does not remain rigid enough for a user to push it through the hole (i.e., valve).

The open configuration between the vascular system and the environment, however, allows two serious clinical problems. First, air embolism into the vascular system which can result in patient injury and/or death. And second, release of potentially infectious bodily fluids (including blood) into the environment, resulting in exposure to the health care provider.

SUMMARY OF THE INVENTION

The invention relates to tear-away and non-tear-away sheath introducers for catheters, methods for making such introducers, and methods for using such introducers. The sheath introducers contain movable valves that are encapsulated in a movable housing that allows the valve to move along the axis of the introducer. As the movable valve and housing travel along the axis, a portion of the hub protrudes past the valve and is exposed. As well, the sheath introducers can also contain a stationary valve and housing that can be opened to expose a portion of the hub when a conduit penetrates the stationary valve. In both instances, the protruding portion of the hub contains a friction-free pathway for a catheter into the sheath introducer. The introducers can therefore be used with any catheter, regardless of the size or material, because of the reduced or eliminated frictional force between the catheter and introducer.

BRIEF DESCRIPTION OF THE DRAWINGS

The following description of the invention can be understood in light of FIGS. 1-23, in which:

FIG. 10 is a side perspective view(s) of the sheath introducer in yet another aspect of the invention;

FIGS. 1-23 presented in conjunction with this description are views of only particular—rather than complete—portions of the devices and associated methods of making and using these devices. Together with the following description, the Figures demonstrate and explain the principles of the devices and associated methods. In the Figures, the thickness of layers and regions are exaggerated for clarity. The same reference numerals in different drawings represent the same element, and thus their descriptions will be omitted.

DETAILED DESCRIPTION OF THE INVENTION

The following description provides specific details in order to provide a thorough understanding of the invention. The skilled artisan, however, would understand that the invention could be practiced without employing these specific details. Indeed, the invention can be practiced by modifying the illustrated method and resulting device and can be used in conjunction with apparatus and techniques conventionally used in the industry. For example, the invention is described as a micro-introducer for small catheters (3F-10F in size), but could easily be adapted for any size of catheter or device regardless of the size or intended use. Further, while the invention is described for use with catheters for vascular access, it could be used with any similar device that is used to grant a physician (or other user) access to a part of the body, whether human or animal.

The invention includes a tear-away or non-tear-away sheath introducer that contains a movable valve and housing that when moved, allows a portion of the hub to protrude through a valve and be exposed. The protruding portion of the hub contains a friction-free pathway for the catheter. Any inducer having these properties can be used in the invention, including the sheath introducer described below and illustrated in the Figures.

The sheath introducer of the invention contains several primary components. First, dilator means used to dilate the vascular system and create a pathway for the catheter. Second, means for sheathing the dilator means to protect it from the vascular system. And third, valve means for keeping the pathway created by the dilator closed until the catheter needs to be inserted.

Figure 1:
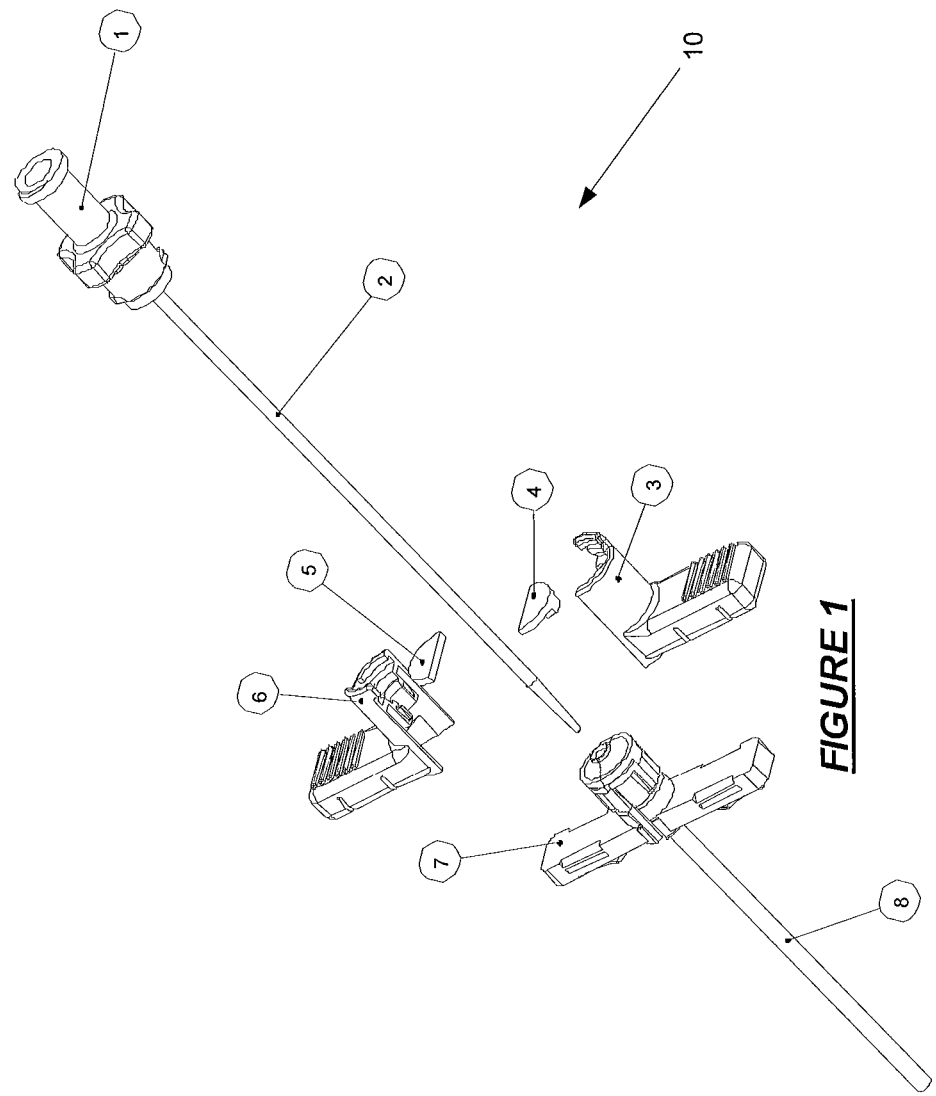
FIG. 1 is a side perspective view(s) of the introducer assembly in one aspect of the invention.

One example of the sheath introducer is illustrated in FIG. 1 where the introducer 10 contains dilation means comprised of a dilator hub 1 and a dilator shaft 2. The dilation means is configured to fit within the sheath means comprised of a sheath hub 7 and a sheath 8. The introducer 10 also contains valve means comprised of a valve with left and right halves (4 and 5) contained within a valve housing having left and right halves (3 and 6) that is attached to the sheath hub 7.

Figure 2:
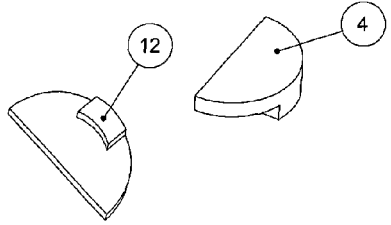
FIG. 2 is a side perspective view of a two-piece flexible valve in one aspect of the invention.
Figure 4:
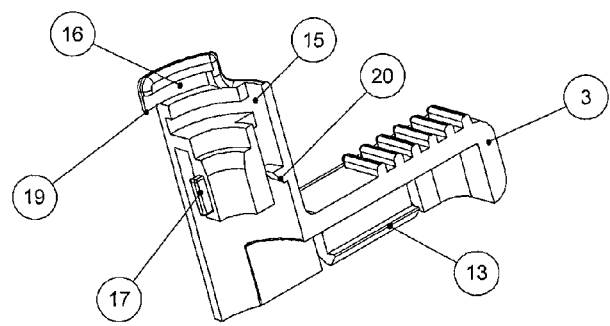
FIGS. 4 and 5 are section views of a valve housing in one aspect of the invention.
Figure 3:
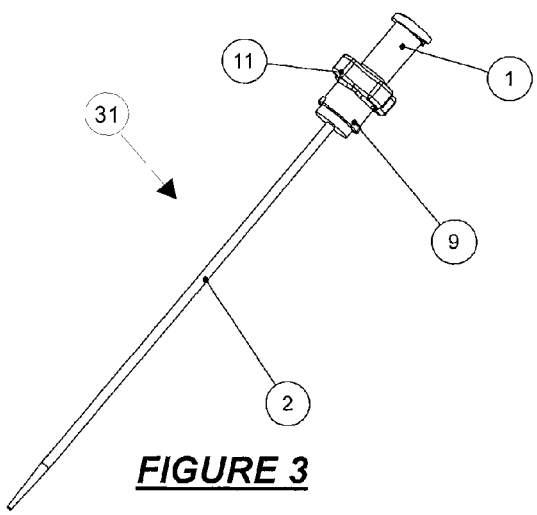
FIG. 3 is a side perspective view of a dilator in one aspect of the invention.
Figure 5:
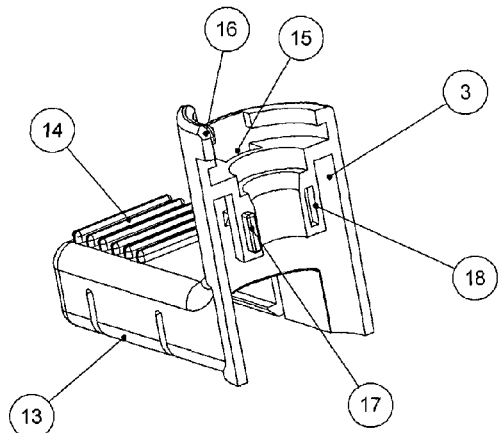

FIGS. 2-5 illustrate detailed views of each of these components. FIG. 2 depicts one half of the valve 4, FIG. 3 illustrates the dilator hub 1, and FIGS. 4-5 shows the different views of one half of the valve housing 3. In FIG. 2, the valve contains retention means for retaining the valve to the valve housing. Any retention means known in the art can be used, including retention member 12 which seats into a corresponding structure in the valve housing such as the valve retention slot 15. The valve has a size and shape substantially the same as the inner part of the valve housing to which it is retained. Accordingly, the valve half 4 depicted in FIG. 2 is substantially circular and with a size that fits within the corresponding inner surface of the valve housing 3 shown in FIGS. 4-5. The valve can be manufactured from any suitable medical material, including flexible materials like silicone or polyurethane.

FIG. 3 depicts one example of a dilator of the introducer 10. The dilator 31 can contain any standard medical luer hub, including a dilator hub 1 with a gripping mechanism (such as finger grips 11) and locking mechanism (such as locking ears 9) as shown in FIG. 3. The locking mechanism 9 locks the dilator 31 into the valve housing by using, for example, the locking channel 16 contained in the valve housing 3 and 6. The dilator 31 also contains a shaft 2 with a tapered section for dilating the vessel into which it is inserted. The dilator 31 can also be manufactured from any suitable medical material, but should be made fairly rigid, yet flexible enough that it can be maneuvered into the desired vessel by a user.

FIGS. 4 and 5 depict one example of the internal geometry of the valve housing 3. The valve housing 3 contains any means for securing the valve housing to the sheath hub 7. In FIGS. 4 and 5, the securing means comprises snap features 13, which secure the valve housing 3 to the sheath hub 7 using the mating snap feature 21 (shown in FIG. 6). Using the securing means keeps the valve housing (and therefore the valve) in a closed position until it is needed to be opened (i.e., such as when the catheter is inserted).

The valve housing 3 also contains any known means for positioning it with the sheath hub 7. An example of this positioning means is depicted in FIGS. 4 and 5, where a guide slot 15 and stop post 20 mate with the guidepost 22 of the sheath hub 7 (shown in FIG. 6). The exterior of the valve housing 3 contains grips 14 that can be employed by the user in the splitting procedure. The valve housing 3 is constructed of any suitable medical material that provides the desired rigidity, such as rigid polymeric materials.

The valve housing 3 can also contain any known interlock mechanism between the two halves of the valve housing. An example of this interlock mechanism is lock 19 that, when the halves are assembled together, serves to maintain uniform travel between both halves of the valve housing. This interlock mechanism can be supplemented with any known mechanism, including the detachable interlock features 17 and 18.

Figure 6:
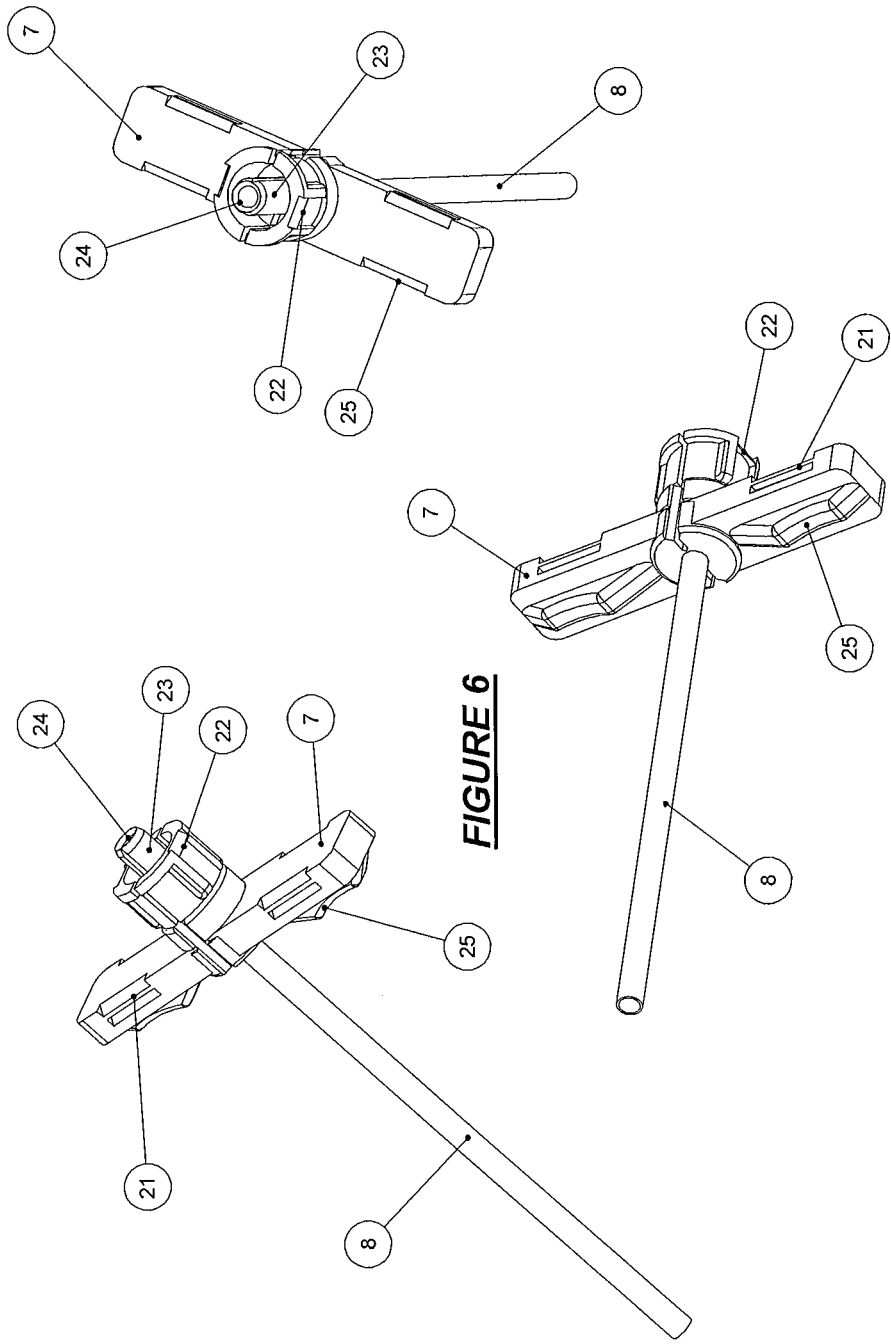
FIGS. 6 and 7 depict the introducer assembly in another aspect of the invention.
Figure 7:
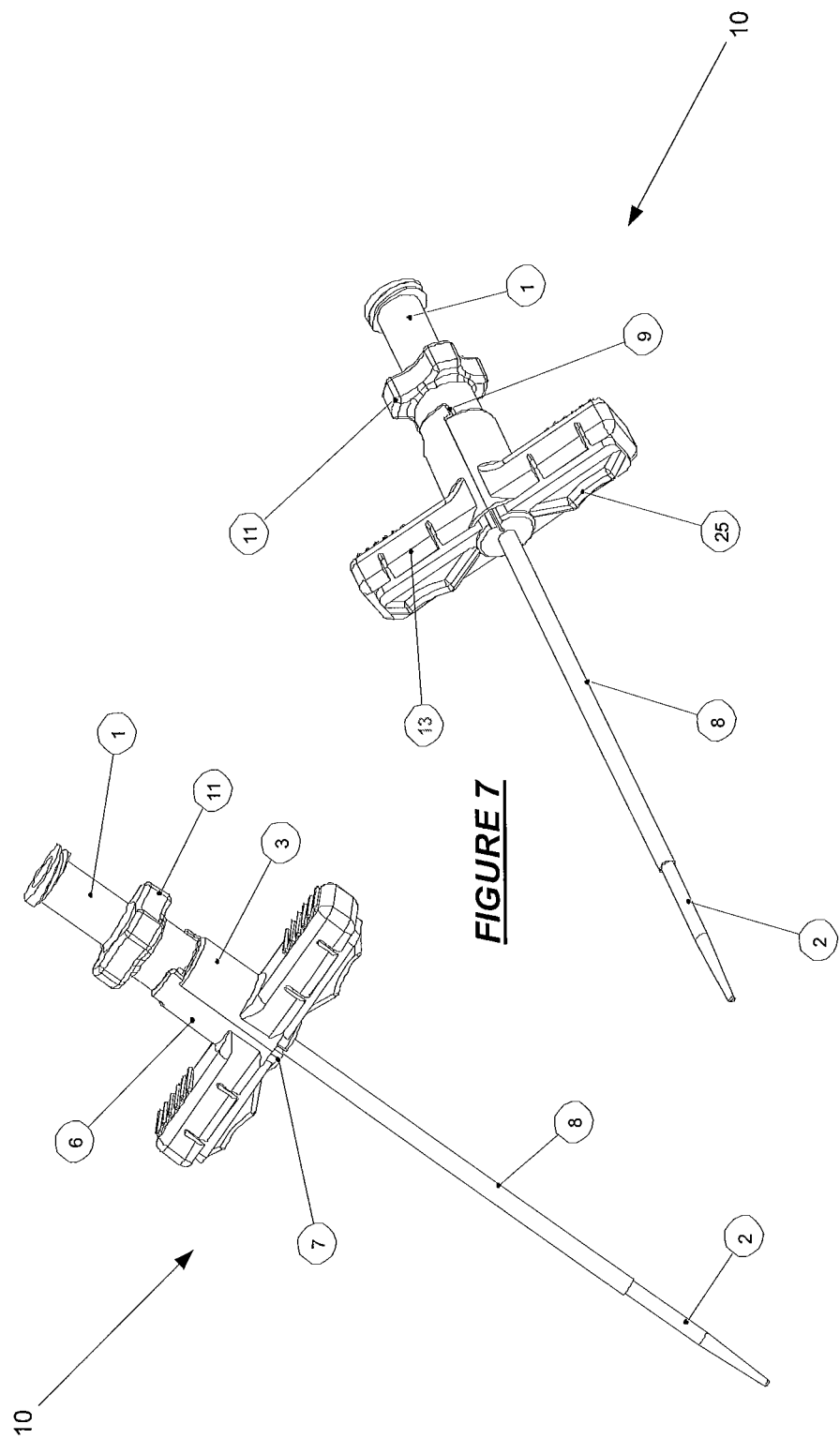

FIGS. 6 and 7 illustrate the various components of the introducer when assembled together. In FIGS. 6 and 7, the sheath hub 7 and the sheath 8 are attached together into an assembly by any attachment means. Examples of suitable attachment means include insert molding or any mechanical attachment, such as a friction fit, locking snap fit, solvent or UV bond.

The sheath hub 7 contains several features for its operation. One such feature includes valve snap fit grooves and edges 21. These two components, along with the snap feature 13, work together to snap the valve housing 3 (and 6) to the sheath hub 7. Of course, any similar mechanism can be used to snap these two components to each other. The sheath hub 7 also contains the guide slot 22, as mentioned above, that guides the valve housing 3 (and 6) and the hub to the correct location relative to each other.

The sheath hub 7 also contains a valve penetration means. The valve penetration means operates to penetrate the two halves of the valve 4 and 5, thereby providing an opening in the valve. Any penetration means known in the art can be used for this function. As depicted in FIGS. 6 and 7, the penetration means comprise penetration member 23 that is configured to fit between the two halves 4 and 5 of the valve. The penetration member 23 opens the two halves 4 and 5 of the valve when it is forced between them by any action which pushes the penetration member 23 through the valve.

The valve penetration means need not physically force (i.e., push) the valve halves 4 and 5 apart to penetrate the valve. In this aspect the penetration member 23 penetrates the valve halves 4 and 5 when the valve housings are pulled apart to expose the penetration member 23. The valve housings 3 and 6 can be pulled apart by the mechanisms described below.

When the penetration member 23 opens the valve in either of these manners, port 24 is exposed. The port 24 is the location where the catheter (or similar device) is inserted. Unlike the conventional introducers where the catheter is forced between the valve (which creates a friction force that must be overcome by a user), the catheter can be inserted in the port 24 of the introducers. The port 24 can be configured to have less friction than that required in conventional devices by providing an inside diameter slightly larger than that of the catheter insertion member. Alternatively, the port can be configured to have substantially no friction ("friction-free") by providing an inside diameter significantly larger than that of the catheter insertion member. As well, the port 24 can be configured to have less or substantially no friction by providing a coating on the inside of the port 24 and/or the outside of the catheter.

The sheath hub 7 also contains activation means. The activation means is used to force the penetration member 23 up through the valve halves 4 and 5, move the valve halves (and housing) down over the penetration member 23, or to pull the valve halves 4 and 5 apart, to thereby open them and expose penetration member 23 containing port 24. Any mechanism that operates in this manner can be use as the activation means. In the sheath hub depicted in FIG. 7, the activation means pulls the valve halves 4 and 5 apart and comprises a reaction force member 25 that is formed on the bottom edge of the sheath hub 7. When pressure is applied to the reaction force member 25 by the user, it depresses the valve housings 3 and 6 and forces the valve halves 4 and 5 apart. Of course, any other known mechanism could be used to push or pull the valve apart.

Figure 8:
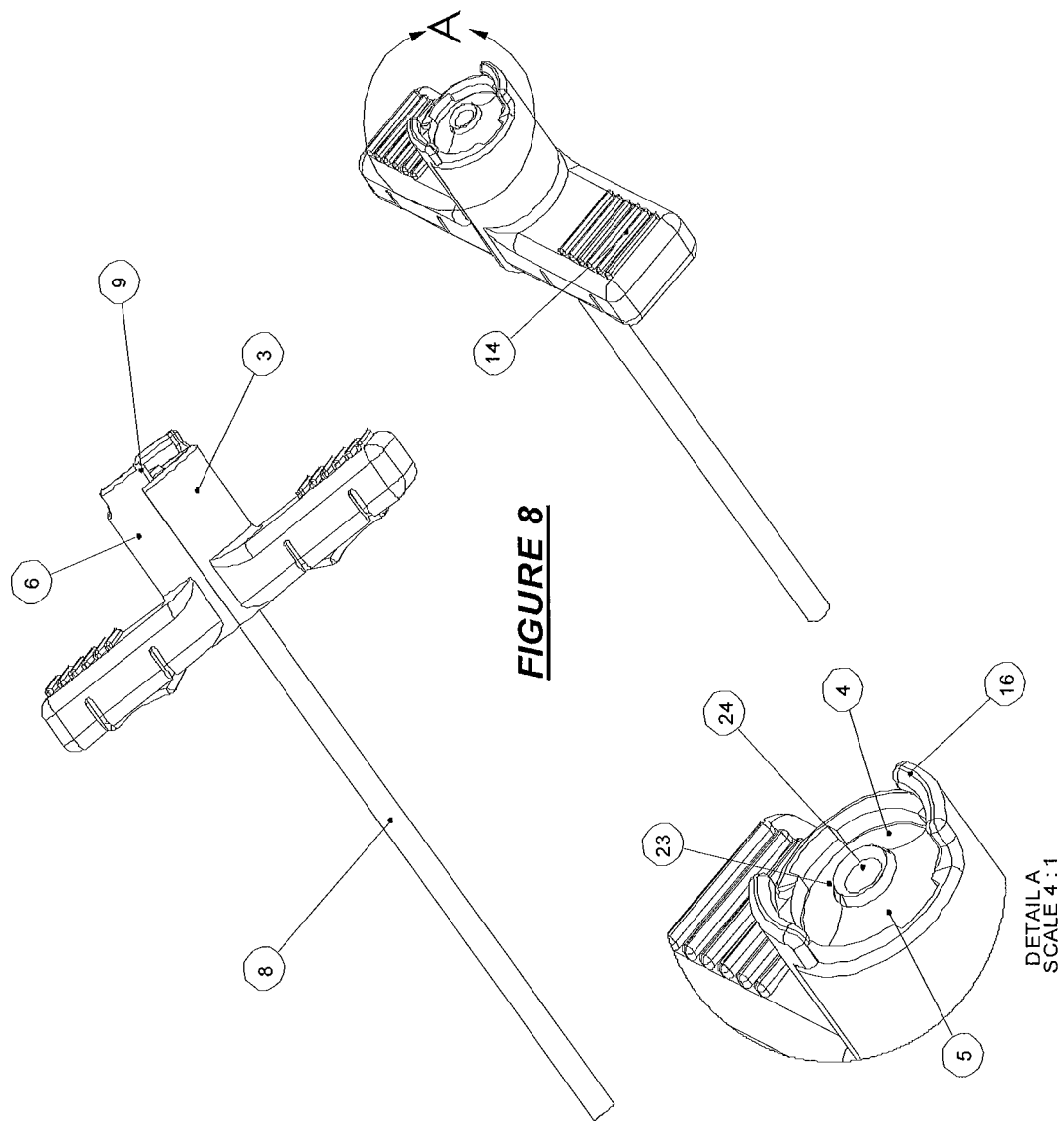
FIG. 8 is a side view(s) of the sheath introducer in another aspect of the invention.

FIG. 8 depicts the introducer in a position ready to accept a catheter. In FIG. 8, the penetration member 23 protrudes out of the valve halves 4 and 5. The penetration member 23 need only protrude enough so that port 24 is exposed enough for a catheter to be inserted. Typically, the port 24 protrudes from about 0.025 to about 0.05 inches above the valve. In one aspect of the invention, the port 24 protrudes about 0.05 inches above the valve.

Figure 9:
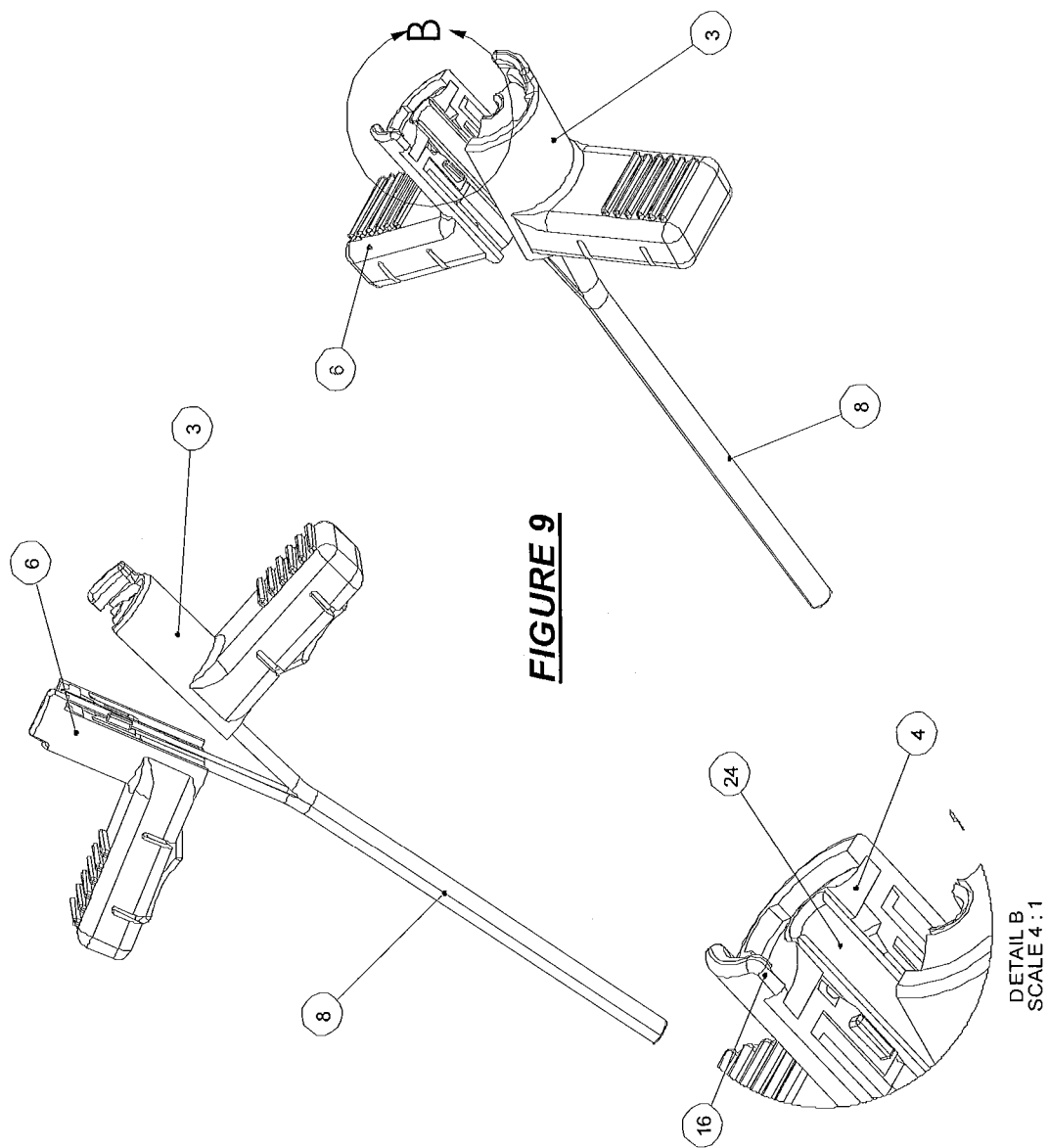
FIG. 9 is a side perspective view(s) of the sheath introducer in even another aspect of the invention.

FIG. 9 depicts one part of a method for using the introducer 10. After the introducer 10 has been inserted into the desired vessel, the catheter (not shown) is inserted through the introducer 10. Then, the user presses on the grips 14 to cause the valve housing 3 and 6 to separate from each other. As the pressing continues, the valve halves 4 and 5 and the sheath hub 7 then separate from each other. Once this initial separation has occurred, the user can continue pull on the ends of the separated portions to continue separating the introducer 10.

FIG. 10 illustrates another part of a method for using the introducer 10. In step 1, the introducer 10 has been inserted in the desired part of the vascular system, i.e., the desired vessel. Next, as shown in step 2, the dilator is then removed from the introducer 10. As shown in step 3, removing the dilator still leaves the valve in a closed position. Next, using the actuating mechanism a user makes the penetration member 23 penetrate the valve in any of the methods described above so that valve is opened with the port 24 exposed. Then, the catheter (not shown) is inserted into the introducer as shown in step 4. Finally, the introducer is removed by the splitting procedure as shown in step 5.

In some embodiments, the introducer can be configured so that the valve is stationary. In these embodiments, the stationary valve can be opened to expose a portion of a hub when conduit means penetrate the stationary valve. With a portion of the hub exposed, the catheter can then be inserted as described above.

Figure 22:
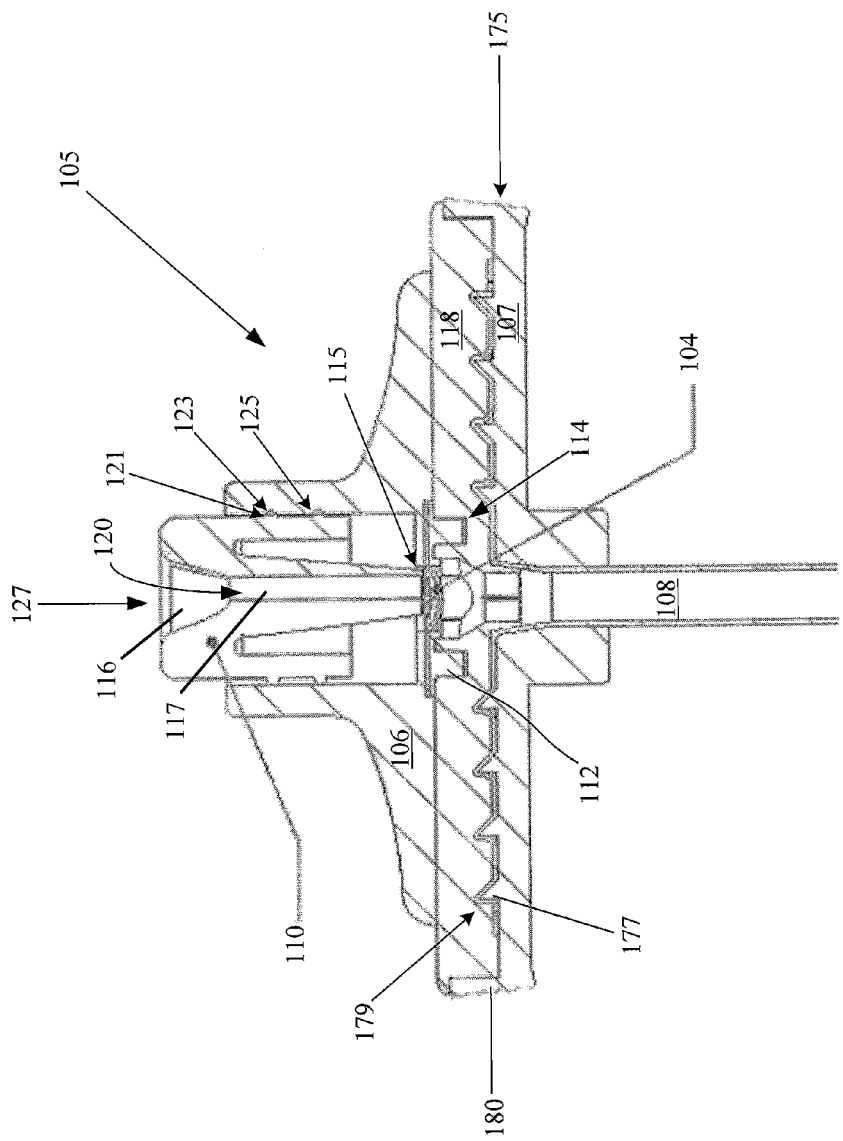
FIGS. 22-23 illustrate an introducer containing a stationary valve that is opened by a movable conduit.
Figure 23:
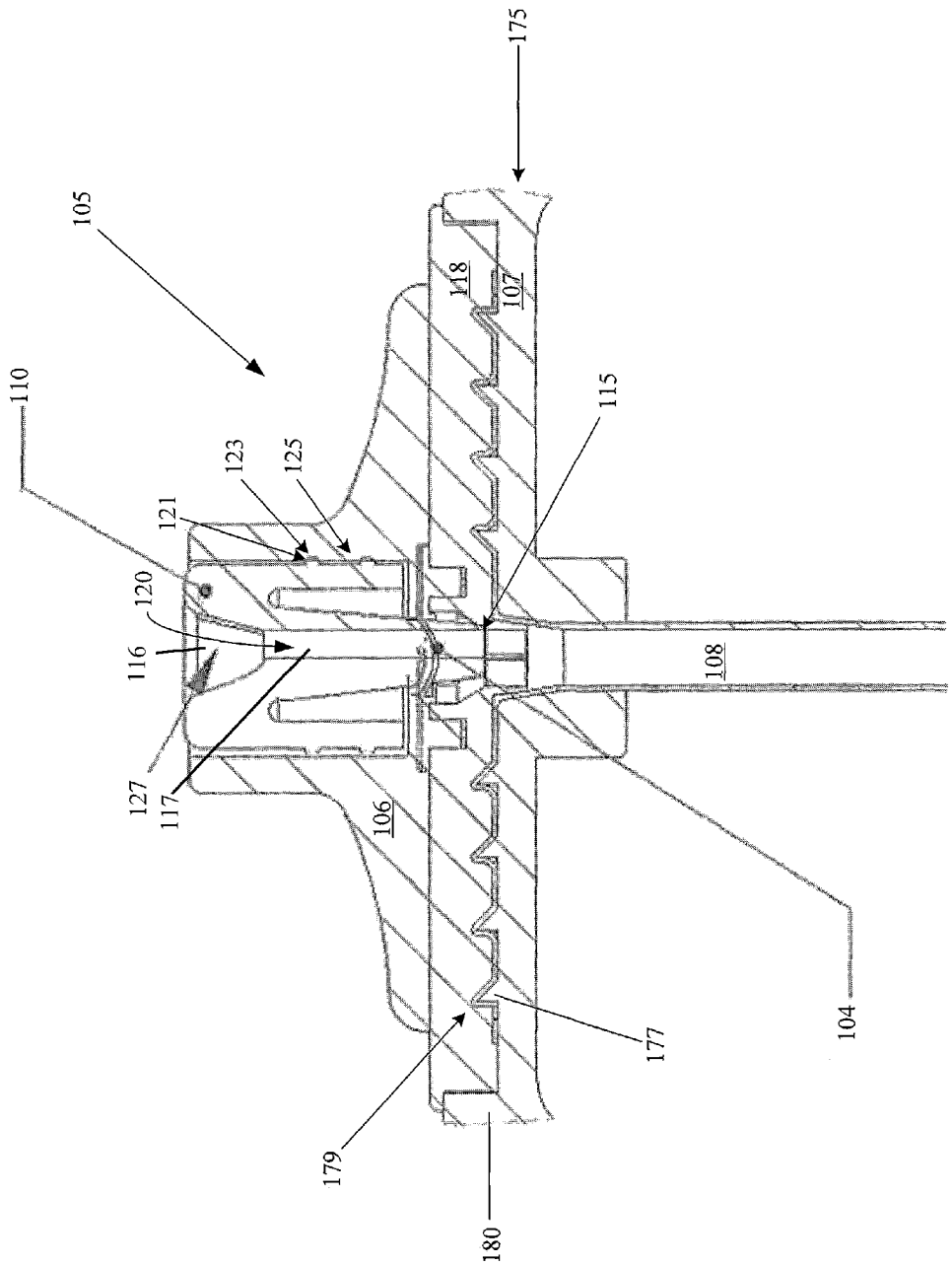

One example of these embodiments is illustrated in FIGS. 22-23. FIG. 22 depicts an assembled introducer 105 without a dilator. The assembled introducer 105 contains a sheath hub bottom 107 containing a sheath hub top 108, and valve means comprised of a stationary valve 104 contained within a valve housing 106. The assembled introducer 105 also contains conduit means (i.e., conduit 110) that can move along the axis of the assembled introducer 105. The conduit member 110 includes a cylindrical portion 116 and a conical portion 117.

The valve 104 can be configured to be stationary within the assembled introducer 105 using any known mechanism. In the embodiments illustrated in FIGS. 22-23, the valve 104 is configured to be stationary by matching the extensions 112 of the valve 104 with corresponding indentations 114 within a press fit generated between the sheath hub top 118 and valve housing 106. In other instances, though, the extensions 112 could be configured to match indentations made in the valve housing 106 (not shown). In yet other instances, the valve 104 can be configured to be stationary by means of any known adhesive.

The valve housing 106 houses the stationary valve 104 and therefore the bottom of the valve housing 106 can be configured to substantially match the shape of the valve 104. As well, since the valve housing 106 is located on the sheath hub top 118, the bottom of the valve housing 106 can be configured to substantially match the upper surface of the sheath hub top 118. As depicted in FIG. 22, these matching surfaces can be substantially flat. But any other matching shapes for these surfaces can be used, including ridged, notched, or an interlocking snap fit.

The valve housing 106 also surrounds the conduit means (i.e., conduit 110). Accordingly, the inner surface of the valve housing can be configured to substantially match the outer surface of the conduit 110. As depicted in FIG. 22, these two matching surfaces can be configured as substantially circular in shape. But other geometries for these surfaces can be used, including substantially rectangular, substantially oval, substantially polygonal, or a male/female keyway.

The conduit 110 moves along the axis of the assembled introducer 105 from a first position shown in FIG. 22 to a second position shown in FIG. 23. In the first position, the bottom 115 of the conduit 110 remains above the closed valve 104. In the second position, the bottom 115 of the conduit 110 has pierced the valve 104 and forced the valve 104 into an open position. With the valve 104 in this open position, a catheter can be inserted though the conduit 110 and into the sheath 108.

In other embodiments, the conduit 110 can move into an intermediate position anywhere between the first and second positions. The intermediate position can be selected so that the valve 104 is opened by any desired amount. For example, the intermediate position for the conduit 110 can be selected so that a partially opened valve would allow only a small amount of blood to be exposed, ensuring that the assembled introducer 105 was located correctly in a vein.

The conduit means can have any configuration allowing it to operate in this manner. Thus, the outer surface of the conduit 110 can be configured to be slightly smaller than the inner surface of the valve housing 106, allowing the conduit 110 to move easily relative to the valve housing 106. If desired, additional mechanisms like depth control detents, springs, or coatings can be used to increase—or, if necessary, decrease—the ability of the outer surface of the conduit to move relative to the inner surface of the valve housing 106.

In some instances, the outer surface of the conduit 110 and the inner surface of the valve housing 106 can be configured so that the conduit can be retained in the first and second positions. Any retaining means known in the art can be used, such as markings, depth control detents, springs, threads or the retaining means illustrated in FIGS. 22-23. In these Figures, the retaining means comprises at least one notch 121 on the outer surface of the conduit 110 that substantially matches indentations 123 and 125 on the inner surface of the valve housing 106. The two (or more) sets of indentations are located where the notch 121 will insert when the conduit 110 is in the first and second positions.

The bottom 115 of the conduit 110 can be configured so that it pierces and opens the stationary valve 104. Thus, the bottom 115 of the conduit can be configured with any shape that will operates in this manner. In some instances, the bottom 115 is typically given a substantially pointed or substantially tapered shape. The bottom of the conduit can therefore initially open the valve and as the conduit moves further down, the opening in the valve becomes wider and wider allowing for a substantially friction-free passage way through the valve. In some instances, the bottom of the conduit can be rounded to prevent damage to the valve.

The top 127 of the conduit 110 can be configured with any shape so that it guides the placement of the catheter. One example of such a shape is depicted in FIGS. 22 and 23 where the top of the conduit comprises a substantial conical shape. The conical shape guides the placement of the catheter through the top of the conduit and into the inner chamber 120 of the conduit 110. The conical shape can, in certain instances, be smooth and rounded so that it is easier to be pushed by a user to open the valve.

Once the assembled introducer 105 is located in the desired location, the user can open the valve easily by pressing on the top of the conduit means. This action forces the conduit 110 from the first position into the second position, and opens the valve. The user can then place the tip of a catheter in the top of the conduit. As the user pushes on the catheter, the tip is guided from the top of the conduit 110, though the inner chamber 120, past the opened valve, out the bottom of the conduit, and then into the sheath 108.

Figure 11:
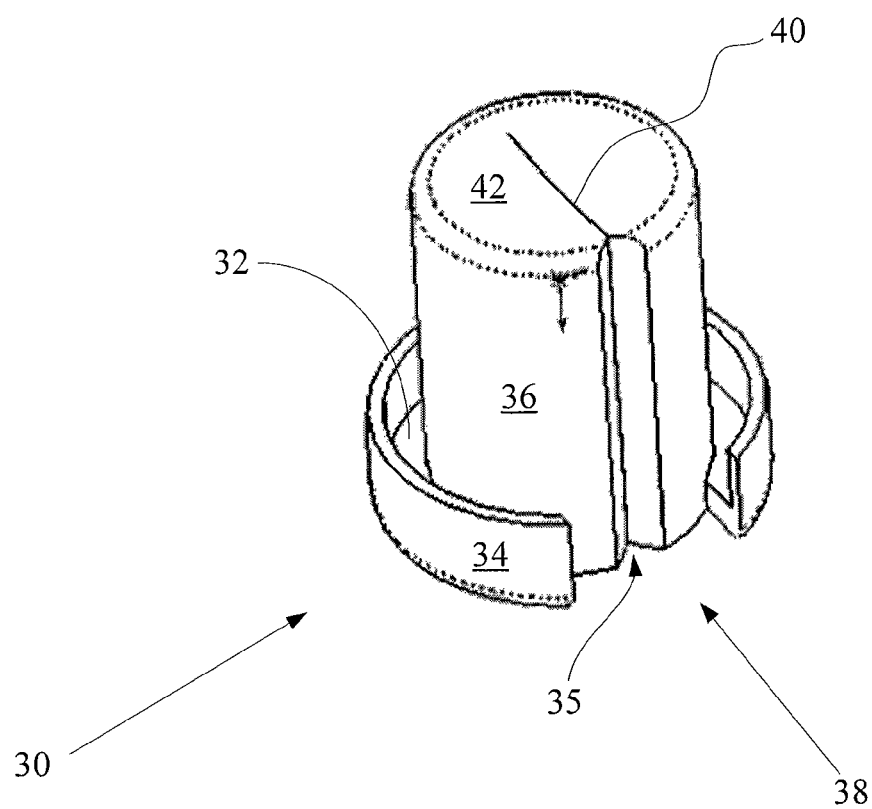
FIGS. 11-12 show a single-piece valve in another aspect of the invention.
Figure 12:
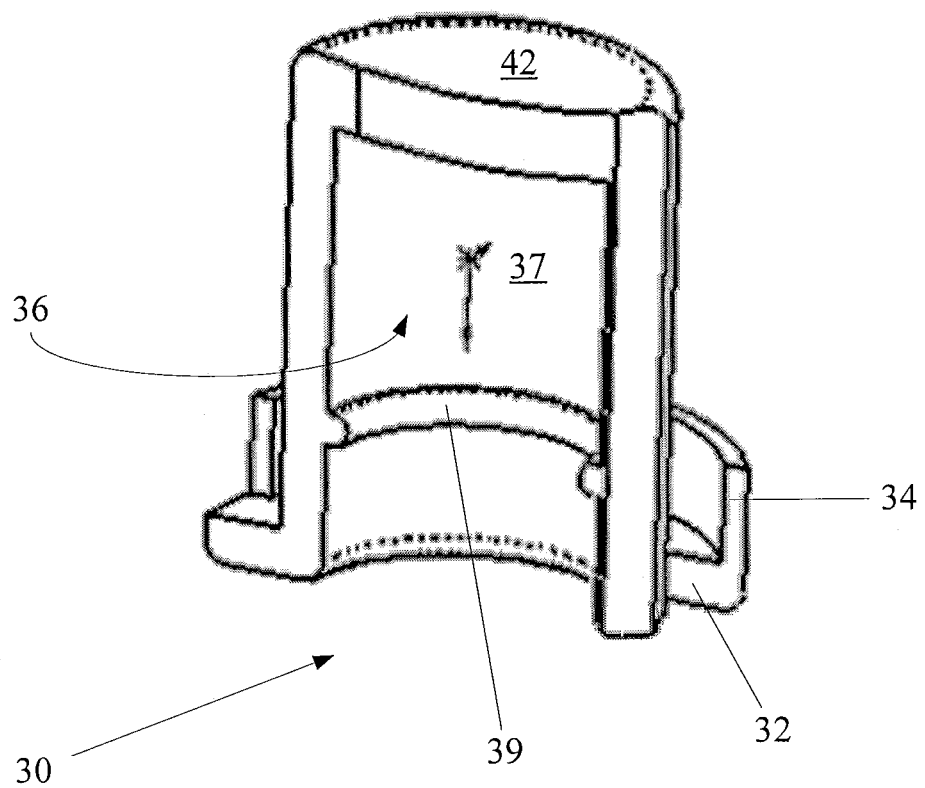

The introducers described above can be modified and enhanced with several optional features. One of these modifications is a modified valve 30 as depicted in FIGS. 11 and 12 that comprises a base 32, extensions 34, and channel portion 36. The base 32 of the valve 30 is configured with a size and shape substantially similar to the valve housing in which the valve 30 rests. The valve 30 can optionally contain an indentation 35 of any shape and size that will help the valve split.

The extensions 34 are designed to extend upwards from the valve 30 towards the dilator of the introducer. Like the base 32, the extensions 34 will abut the valve housing, but the sides rather than the bottom. Accordingly, the size and shape of the extensions 34 are selected to substantially match the inner surface of the valve housing which will enclose the valve 30. The extensions 34 contain a notch(es) 38 that correspond to the notches 50 provided in the protruding member 41 (as described below).

The channel portion 36 of the valve 30 also extends in an upward direction toward the dilator of the introducer. As shown in FIG. 12, the inner surface 37 of the channel portion 36 will abut the outer surface of the outside of the protruding member 41 and is accordingly given a size and shape substantially matching the protruding member 41. The length of the channel portion 36 is also selected to substantially match the protruding member 41 so that port 44 can be exposed when desired.

Figure 13:
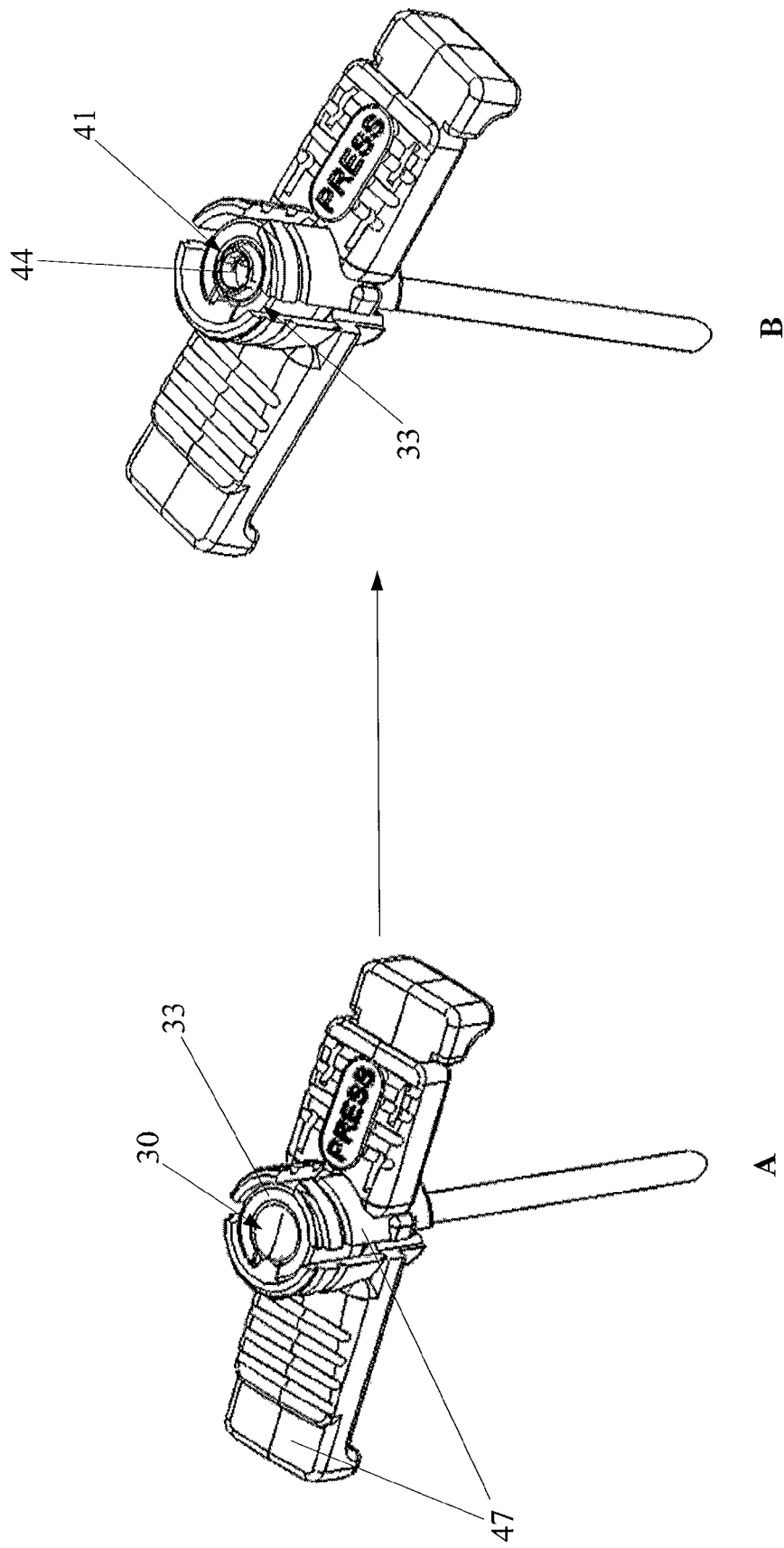
FIGS. 13-14 depict view(s) of the single-piece valve and sheath hub in another aspect of the invention.

The upper surface 42 of the channel portion contains a slit 40. The slit 40 does not extend the entire way across the channel portion 36 and so is a non-tear away slit. The slit 40 is held in a closed or sealed position (position A in FIG. 13) by the valve housing and sheath hub. The slit 40 moves into an open position B when the protruding member 41 moves upward through the channel portion 36 and then up through the slit 40 (or the valve 30 moves downward over the member 41) as depicted in FIG. 13. Of course, as described above, the valve 30 can be pulled apart to expose the protruding member 41 rather than forced apart.

The channel portion 36 of the valve 30 can also operate as a sealing means around the protruding member 41. The sealing means helps provide a seal between the vascular system and the environment when the protruding member 41 has forced the slit 40 open. This sealing function is illustrated in FIG. 13 where the protruding member 41 is shown in its extended state, i.e., protruding above the valve 30. The channel portion 36 fits snugly around protruding member 41 so that it provides a seal. Optionally, a coating can be added to the inside of the channel portion 36 and/or the outside of the protruding member 41 to increase this sealing function. As shown in FIG. 12, the channel portion 36 can optionally contain a ring sealing member(s) 39 to increase the sealing function.

The advantage of valve 30 is that it can also serve as a flash-back chamber. If the valve 30 (and associated parts of the hub sheath) is made from a translucent or transparent material, it allows the user to view the inside of the valve 30. If sheath introducer 10 is placed in the proper location (i.e., in the venous system), blood will enter the valve chamber resulting in a red color as an indication that the sheath introducer is placed correctly. Using a translucent or transparent material for the valve 30 therefore allows the user to look through the valve and determine whether this red color is showing.

Figure 14:
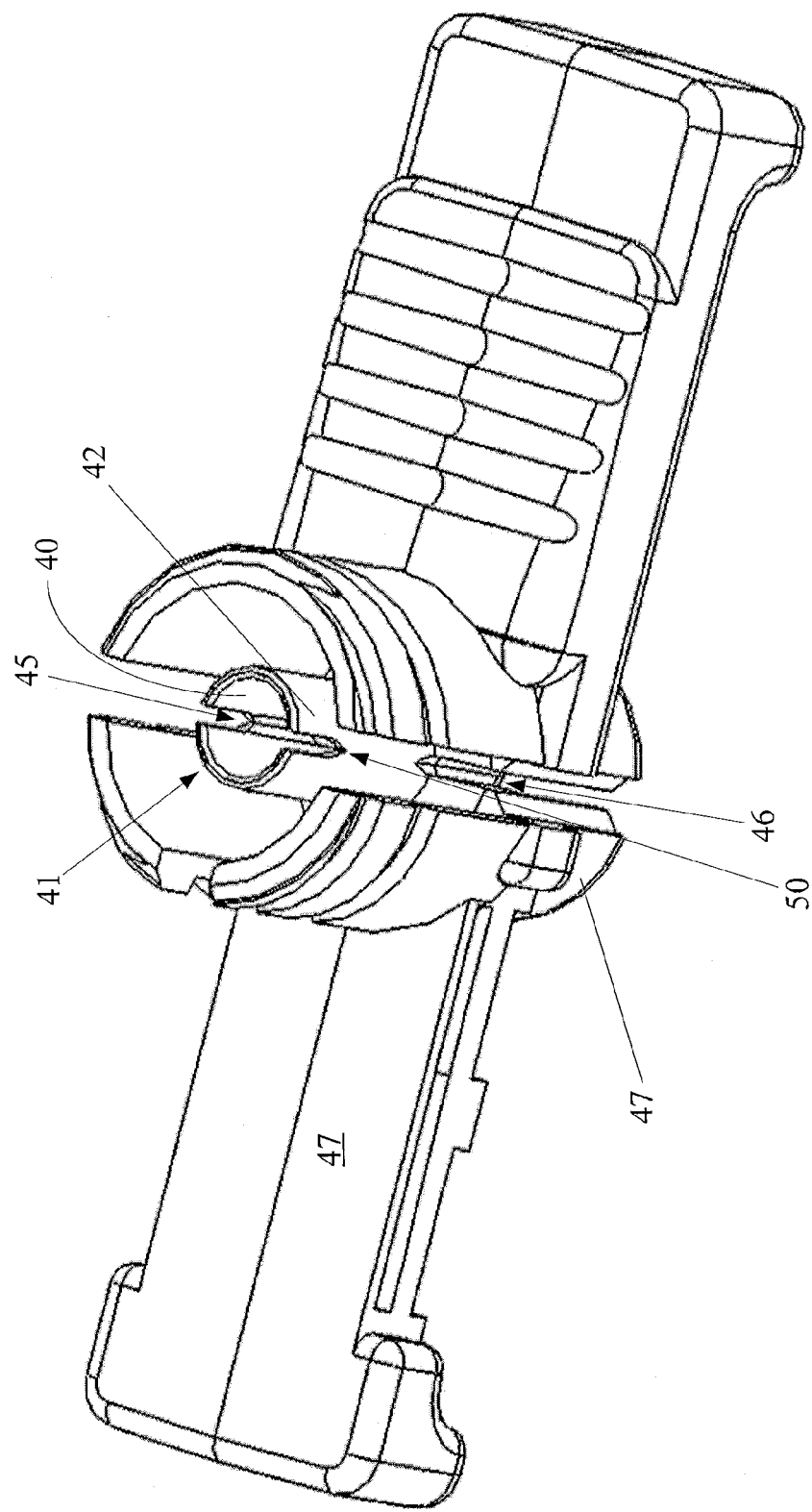

As mentioned above, a seal can be formed between the channel portion 36 and the protruding member 41. To help improve the seal between these two components, the protruding member 41 can be modified by providing stress risers (45 and 46) on the inside 40 and the outside 41 of the protruding member 41 as shown in FIG. 14. The internal stress riser 46 provides a smooth surface at the interface with the valve ring sealing member 39. As noted above, the valve ring sealing member 39 can provide a seal as the valve translates along the stem. Moving from the bottom to the top of the protruding member 41, the riser(s) 45 begin on the outside and then move to the inside 46, allowing the splitting mechanism (crack) to progress while maintaining a smooth outer surface between the valve ring sealing member 39 and the protruding member 41.

The stress riser 45 begins on the bottom of the sheath hub 47 and continues along the outside of the sheath hub until the stress riser 45 reaches a point below the initial location of the valve ring sealing member 39. At that point, the stress riser 46 moves to the inside of the protruding member 41 and then continues to the notch 50. The depth and width of the stress risers 45 and 46 are selected depending on the required separation force.

Another function of the stress risers 45 and 46 are to act as an initiator in the splitting process. By their nature, the stress risers are the beginning of a split in the hub sheath 47 and, therefore, can be used to make the splitting process easier. Accordingly, the stress risers 45 and 46 are located substantially on the axis where the introducer 10 will be split.

Another optional modification that can be made to the sheath introducer comprises notches 50 in the upper portion of the protruding member 41 that remain above the valve 30 in the extended position. The notches 50 give the protruding member 41 additional length to extend past the valve 30 while at the same time not adding additional length to the stress risers 45 and 46. Such a configuration adds length to the protruding member 41 without increasing the cracking force needed to split the introducer 10.

As shown in FIG. 14, the notches 50 are generally made to correspond with the same location as the stress risers 45 and 46, i.e., substantially along the axis of the expected split. The notches 50 can have any shape that results in a concentration of the stress force. Examples of such shapes include substantial "V" shape or the substantial rectangular shape shown in FIG. 14.

Figure 15:
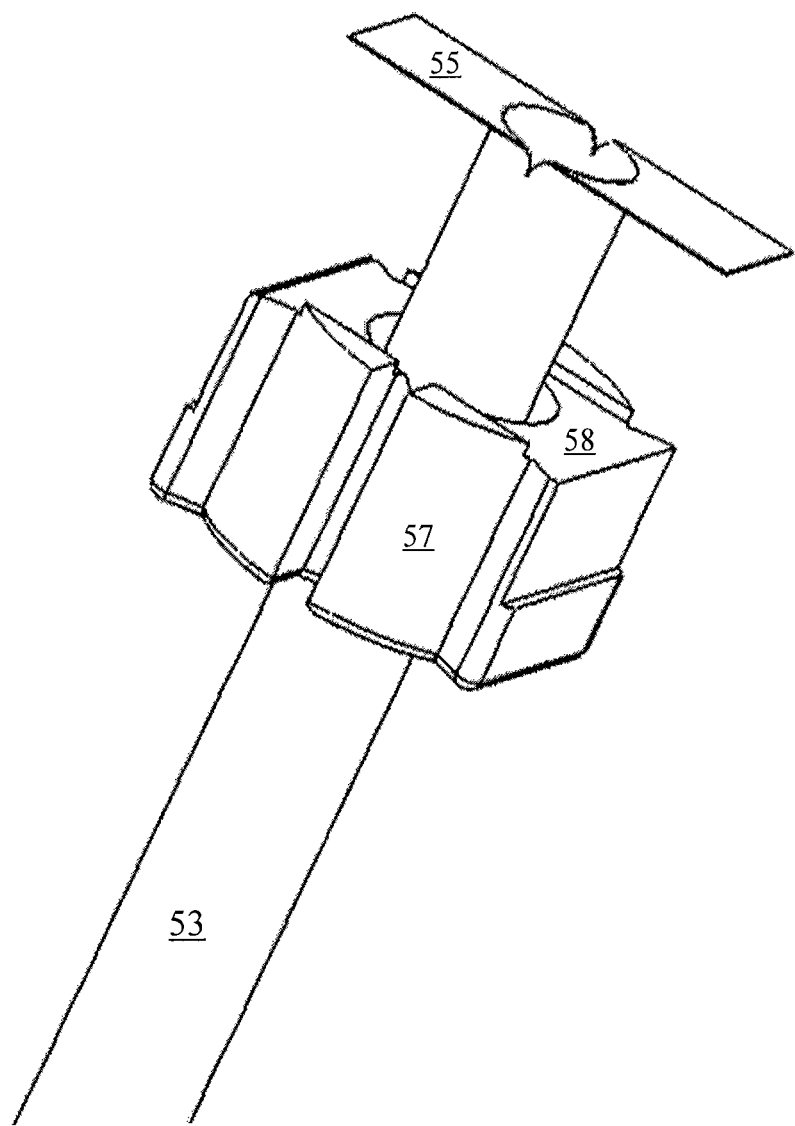
FIGS. 15-17 depict view(s) of methods of increasing the attachment between the sheath and the sheath hub in another aspect of the invention.
Figure 16:
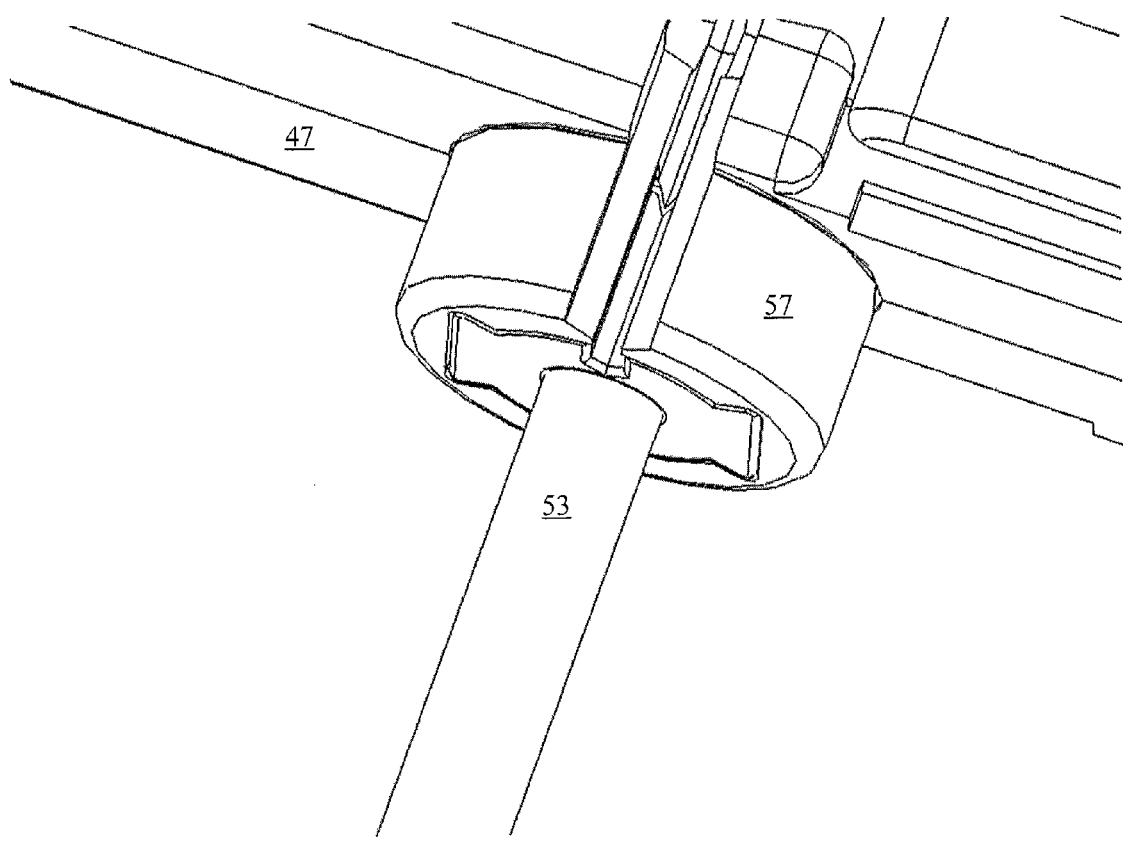

The sheath hub 47 can also be optionally modified to increase the attachment between the sheath hub 47 and the sheath 53. One manner to increase this attachment is depicted in FIGS. 15 and 16. In FIG. 15, the sheath has been modified to contain a sheath cap 57 with an interlocking fit between the sheath 53 and the sheath cap 57. The sheath cap 57 contains grooves 58 which provide a location for the split ends 55 of the sheath 53 when the sheath is inserted though the sheath cap 57. The ends of the split sheath fold around the sheath retention cap 57 with their location maintained in the grooves 58. Once the sheath retention cap 57 is assembled into the mating geometry of the sheath hub 47 as shown in FIG. 16, it locks the ends 55 of the split sheath tightly into the hub 47. The sheath cap 57 is then affixed to the sheath hub 47.

Figure 20:
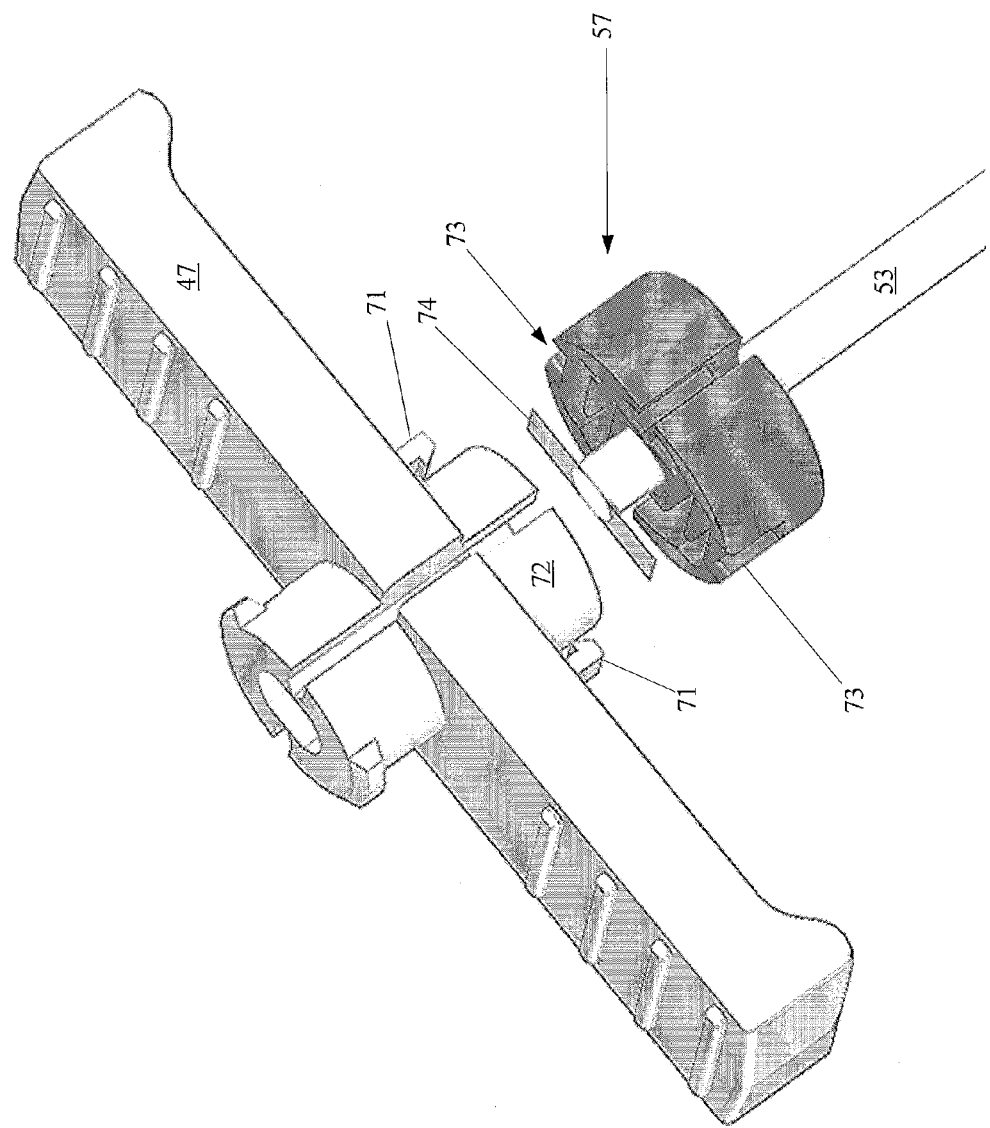
FIGS. 20-21 depict view(s) of methods of increasing the attachment between the sheath and the sheath hub in another aspect of the invention.

In some embodiments, the sheath cap 57 can affixed to the sheath hub 47 by means of a thermal, solvent or UV bond. In other embodiments, the sheath cap 57 can be affixed to the sheath hub 47 using a mechanical connection as known in the art, including a friction fit, snap fit, or ultrasonic weld. One example of such a mechanical connection is illustrated in FIG. 20, where the sheath hub 47 had been provided with a connector 72 containing male connections 71. The sheath cap 57 has also been provided with a corresponding shape and size that will mate with the connector 72, including female connections 73. When the sheath cap 57 is moved towards the sheath hub 47, the male connection 71 slides into the female connection 73 and attaches the hub 47 and the cap 57 to each other. Because of its shape, the cap 57 will also mate with the connector 72 and can be configured, as shown in FIG. 20, to retain the ends 74 of the sheath 53 between them.

Figure 21:
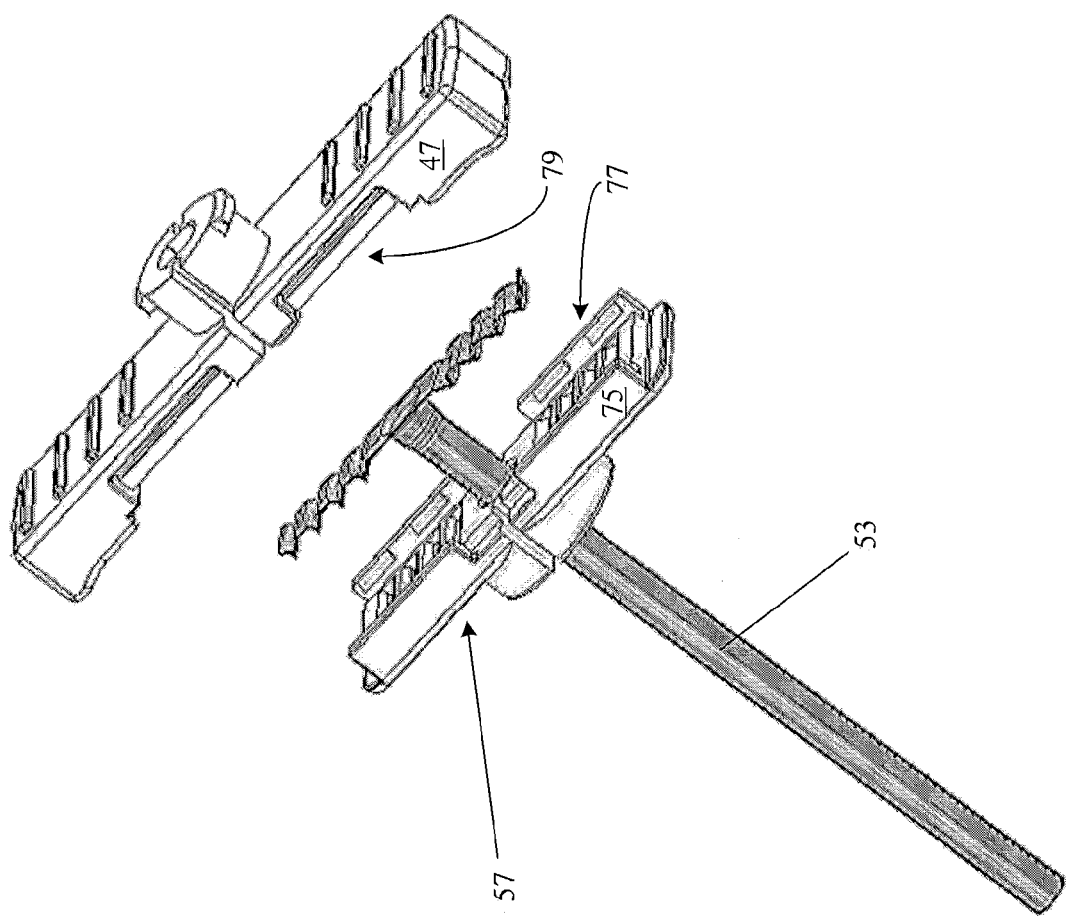

Another method to increase the attachment sheath hub 47 and the sheath 53 is illustrated in FIG. 21. As shown in FIG. 21, the sheath cap 57 has been modified to contain extensions 75 that run substantially parallel to the body of the sheath hub 47. The extensions 75 have been configured to substantially match the body of sheath hub 47. Likewise, the body of sheath hub 47 has been configured to match the extensions of sheath cap 57. Although many matching configurations can be used, the extensions 75 contain ridges 77 that will substantially match notches 79 in the sheath hub. When the sheath cap 57 is moved towards the sheath hub 47, the ridges 77 slides into the notches 79 and attaches the hub 47 and the cap 57 to each other.

A similar, but different, configuration is depicted in FIGS. 22-23. In these Figures, the sheath hub bottom 107 has been modified to contain extensions 175 that run substantially parallel to the body of the sheath hub top 118. The extensions 175 have been configured to substantially match the body of sheath hub top 118. Likewise, the body of sheath hub top 118 has been configured to match the extensions of sheath hub bottom 107. Although many matching configurations can be used, the extensions 175 contain ridges 177 that will substantially match notches 179 in the sheath hub top 118 and then wrap over the ends 180 of the sheath hub bottom 107. When the sheath hub bottom 107 is moved towards the sheath hub top 118, the ridges 177 slides into the notches 179 and attaches the sheath hub top 118 and the sheath hub bottom 107 to each other, with the wrapping portions of the sheath hub bottom 107 aiding the attachment.

Figure 17:
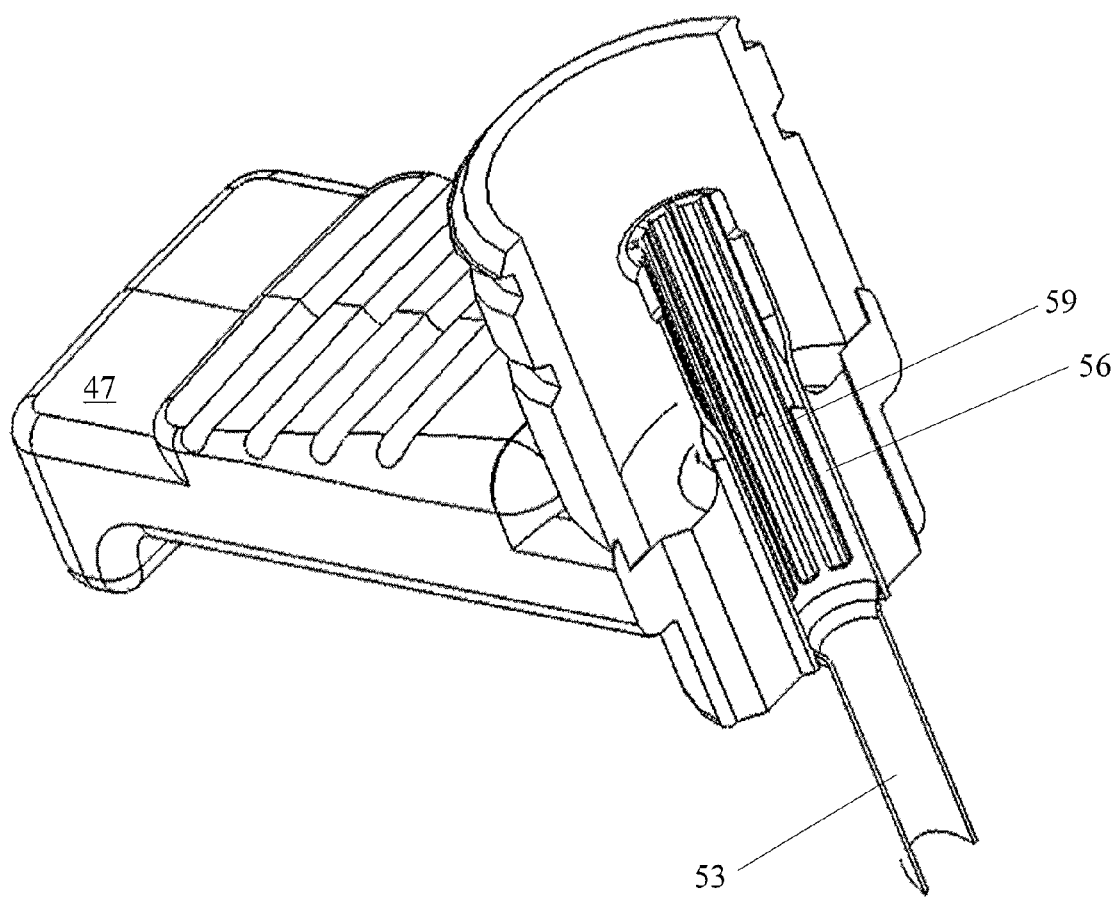

Alternatively, another method to increase this attachment is depicted in FIG. 17. In FIG. 17, the sheath hub 47 has been modified to encapsulate an end portion of the sheath 53. This encapsulation is performed so that ridges 59 overly the end 56 of the sheath 53, thereby retaining the end of the sheath underneath the ridges.

Figure 18:
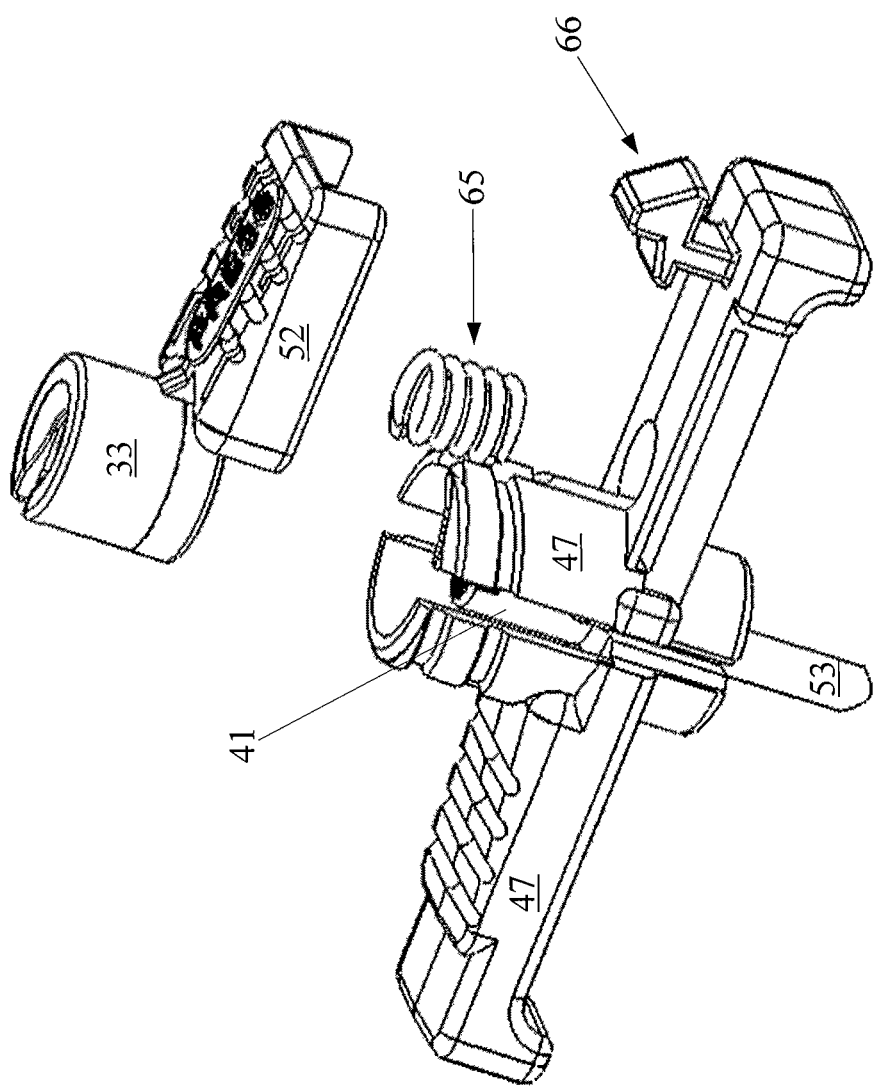
FIG. 18 shows the operation or the sheath introducer in one aspect of the invention.
Figure 19:
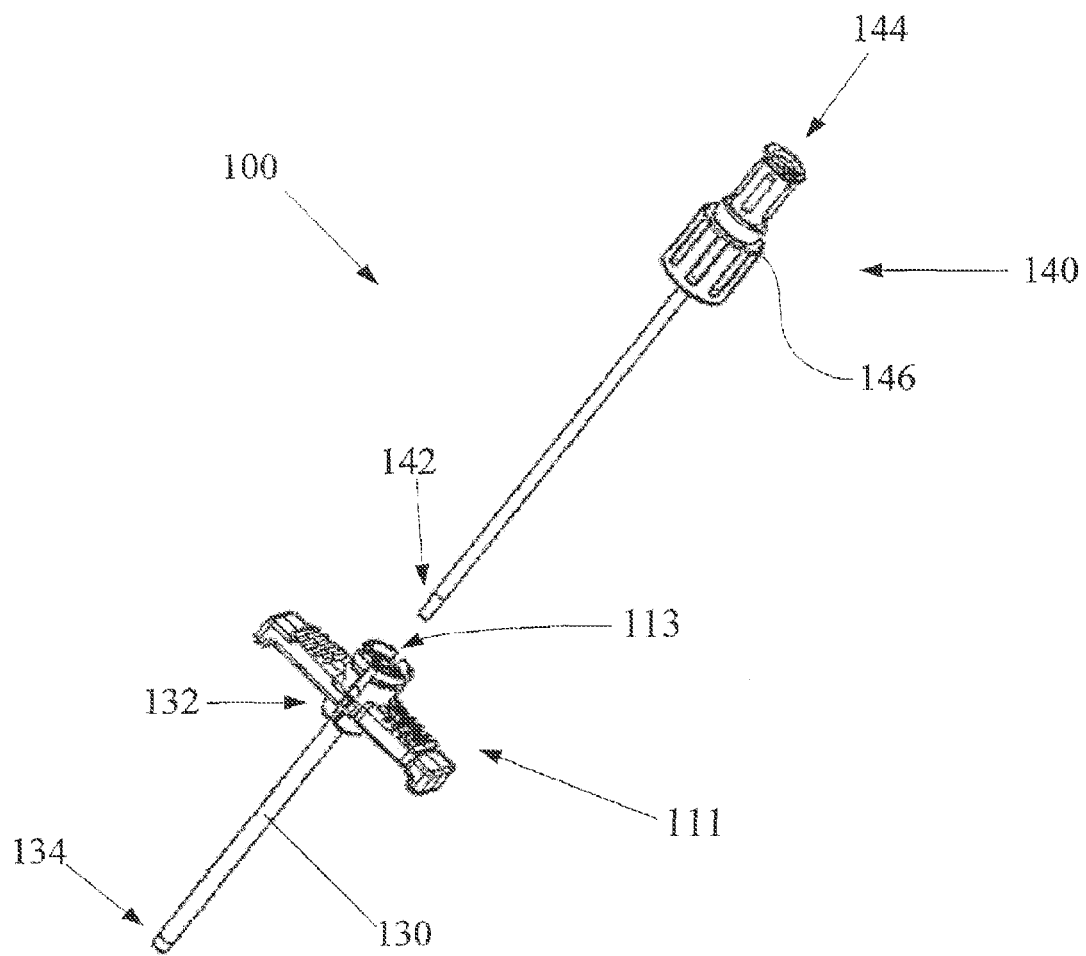
FIG. 19 illustrates a conventional sheath introducer.

In yet another modification, the sheath introducer can be provided with means for separating the valve housing 33 away from the sheath hub 47. Any known means for forcing these two components apart can be used in the invention, including leaf spring, coil spring, hinge, and/or a mechanical lever. As depicted in FIG. 18, the forcing means comprises a spring 65. In its compressed state, the valve housing 33 and the sheath hub 47 are attached to each other by any mechanism, such as the snap features 13 and 21 mentioned above and/or the lever 66. When the valve housing 33 and the sheath hub 47 are attached, the valve 30 remains closed. The moment the user separates the sheath hub 47 from the valve housing 33 by pressing on the grip section 52 (and/or disengaging the lever 66), the spring 65 is released from its compressed state and these two components separate from each other.

One result of the separation of these two components is the movement of valve 30 relative to the protruding member 41. When these two components are attached to each other, the spring is compressed and the valve 30 slides down the protruding member which then opens the slit 40 of the valve 30. When these components are separated, the pressure of the spring 65 is released and it returns to the uncompressed state, sliding the valve 30 back up the protruding member and closing the slit 40.

In another modification, the valve housing of the introducer could be engaged by means of a rotary movement along the axis of a threaded member or any other mechanical means to translate the valve housing along the desired path. For example, a mechanical lever, push button, or threaded member could be used in this modification.

In addition to any previously indicated variation, numerous other modifications and alternative arrangements may be devised by those skilled in the art without departing from the spirit and scope of the invention and appended claims are intended to cover such modifications and arrangements. Thus, while the invention has been described above with particularity and detail in connection with what is presently deemed to be the most practical and preferred aspects of the invention, it will be apparent to those of ordinary skill in the art that numerous modifications, including but not limited to, form, function, manner of operations and use may be made without departing form the principles and concepts set forth herein.

What is claimed is:

1. A sheath introducer, comprising:
   a splittable sheath extending from a sheath hub;
   a valve housing coupled to the sheath hub, a stationary valve positioned within the valve housing, the valve housing comprising:
      a continuous inner surface defining a lumen;
      an outer wall enclosing the entire lumen; and
      a proximal opening; and
   a conduit member having a cylindrical portion, the conduit member movable within the valve housing from a first position in which a proximal section of the conduit member extends outside of the proximal opening of the valve housing and the valve is closed to a second position in which a distal end of the conduit member penetrates the valve to open the valve and the proximal section of the conduit member and the cylindrical portion is positioned substantially within the valve housing.

2. The sheath introducer of claim 1, further comprising a retaining means, wherein the conduit member includes a first retaining feature of the retaining means on an outer surface thereof, and wherein a second retaining feature of the retaining means is positioned on the inner surface of the valve housing.

3. The sheath introducer of claim 2, wherein the second retaining feature comprises at least two spaced apart formations on the inner surface of the valve housing to retain the conduit member in different positions with respect to the valve.

4. The sheath introducer of claim 1, wherein the conduit member comprises a substantially rigid material.

5. The sheath introducer of claim 1, wherein the valve comprises a substantially flexible material.

6. The sheath introducer of claim 1, wherein the distal end of the conduit member is a distal end of a conical portion of the conduit member.

7. The sheath introducer of claim 1, wherein a proximal end of the conduit member comprises a passage having a substantially conical shape.

8. A sheath introducer for a catheter, comprising:
   a splittable sheath extending from a sheath hub;
   a valve housing coupled to the sheath hub, a stationary valve positioned within the valve housing, the valve housing having a continuous inner surface defining a lumen and an outer wall enclosing the entire lumen; and
   a conduit member movable with respect to the valve and the valve housing from a first position in which a proximal end of the conduit member extends outside of the valve housing and the valve is closed to a second position in which the conduit member penetrates the valve to open the valve, the conduit member including a conical portion extending distally from a cylindrical portion, the conical portion having an outer diameter at a proximal end thereof less than an outer diameter of the cylindrical portion the conical portion including a tapered section along at least a distal end thereof, a proximal section of the conduit member and the cylindrical portion positioned substantially within the valve housing in the second position.

9. The sheath introducer of claim 8, wherein the conduit member comprises a friction-reduced insertion port.

10. The sheath introducer of claim 9, wherein a distal end of the conical portion of the conduit member comprises a tip that penetrates the valve, and wherein a proximal end of the conduit member comprises a passage having a substantially conical shape.

11. The sheath introducer of claim 8, wherein the valve forms a seal around the conduit member when it is in the second position.

12. A system for inserting a catheter into a body, the system comprising a sheath introducer containing:
   a stationary valve;
   a valve housing, including:
      a continuous inner surface defining a lumen;
      an outer wall enclosing the entire lumen; and
      a proximal opening; and
   a conduit member having a cylindrical portion, the conduit member positioned in the valve housing lumen, the conduit member having a proximal section extending outside of the valve housing from the proximal opening in a first position in which the valve is closed, the conduit member movable within the valve housing lumen from the first position to a second position in which a distal end of the conduit member penetrates the valve to open the valve prior to the catheter being inserted through the sheath introducer to provide a substantially friction-free passage way through the valve, the proximal section of the conduit member and the cylindrical portion positioned substantially within the valve housing in the second position.

13. The sheath introducer of claim 12, further comprising a retaining means, wherein the conduit member includes a first retaining feature of the retaining means on an outer surface thereof, and wherein a second retaining feature of the retaining means is positioned on an inner surface of the valve housing.

14. The sheath introducer of claim 13, wherein the distal end of the conduit member that penetrates the valve is a distal end of a conical portion of the conduit member, and wherein a proximal end of the conduit member comprises a passage having a substantially conical shape.

15. A method for making a sheath introducer, the method comprising:
   providing a stationary valve;
   providing a valve housing including:
      a continuous inner surface defining a lumen;
      an outer wall enclosing the lumen; and
      a first retaining feature associated with the inner surface, the valve positioned in the valve housing distal of the retaining feature; and providing a conduit member in the valve housing lumen, the lumen surrounding the conduit member, the conduit member movable within the valve housing lumen from a first position in which a proximal end of the conduit member extends outside of the valve housing and the valve is closed to a second position in which a distal end of the conduit member penetrates the valve to open the valve, the conduit member including a second retaining feature on an outer surface thereof to cooperate with the valve housing first retaining feature to retain the conduit member in the second position.

16. The method of claim 15, wherein the valve housing retaining feature comprises at least two spaced apart formations to retain the conduit member in an intermediate position between the first position and the second position.

17. The method of claim 15, including providing the distal end of the conduit member with a conical portion, and providing a proximal end of the conduit member with a passage having a substantial conical shape.

\* \* \* \* \*